(12) United States Patent
Esposito et al.

(10) Patent No.: US 8,925,392 B2
(45) Date of Patent: Jan. 6, 2015

(54) SENSORS, INTERFACES AND SENSOR SYSTEMS FOR DATA COLLECTION AND INTEGRATED REMOTE MONITORING OF CONDITIONS AT OR NEAR BODY SURFACES

(71) Applicant: Heapsylon LLC, Redmond, WA (US)

(72) Inventors: Mario Esposito, Redmond, WA (US); Maurizio Macagno, Redmond, WA (US); Davide Giancarlo Vigano', Redmond, WA (US)

(73) Assignee: Sensoria Inc., Redmond, WA (US)

( * ) Notice: Subject to any disclaimer, the term of this patent is extended or adjusted under 35 U.S.C. 154(b) by 0 days.

(21) Appl. No.: 13/753,456

(22) Filed: Jan. 29, 2013

(65) Prior Publication Data

US 2013/0192071 A1 Aug. 1, 2013

Related U.S. Application Data

(60) Provisional application No. 61/592,333, filed on Jan. 30, 2012, provisional application No. 61/747,877, filed on Dec. 31, 2012.

(51) Int. Cl.
| | |
|---|---|
| *G01L 5/00* | (2006.01) |
| *A61B 5/103* | (2006.01) |
| *A43D 1/02* | (2006.01) |
| *A61B 5/00* | (2006.01) |
| *A61B 5/01* | (2006.01) |

(52) U.S. Cl.
CPC .............. *A61B 5/1036* (2013.01); *A43D 1/027* (2013.01); *A61B 5/1038* (2013.01); *A61B 5/6807* (2013.01); *A61B 5/6831* (2013.01); *A61B 5/002* (2013.01); *A61B 5/01* (2013.01); *A61B 2560/0223* (2013.01); *A61B 2560/045* (2013.01); *A61B 2562/227* (2013.01)
USPC ...................................................... 73/862.01

(58) Field of Classification Search
USPC ...................................................... 73/862.01
See application file for complete search history.

(56) References Cited

U.S. PATENT DOCUMENTS

| | | | |
|---|---|---|---|
| 5,546,955 A | | 8/1996 | Wilk |
| 5,642,096 A | * | 6/1997 | Leyerer et al. ............. 340/573.1 |

(Continued)

FOREIGN PATENT DOCUMENTS

| | | |
|---|---|---|
| DE | 10314211 A1 | 11/2003 |
| EP | 1198197 B1 | 5/2007 |

(Continued)

OTHER PUBLICATIONS

Commonwealth Scientific and Industrial Research Organisation, et al., "International Search Report and Written Opinion," Int'l Patent Application No. PCT/AU2008/001245, filed Aug. 22, 2007 (Oct. 24, 2008).

(Continued)

*Primary Examiner* — Lisa Caputo
*Assistant Examiner* — Octavia Hollington
(74) *Attorney, Agent, or Firm* — Ann W. Speckman; Speckman Law Group PLLC

(57) ABSTRACT

Sensing devices including flexible and stretchable fabric-based pressure sensors, may be associated with or incorporated in garments intended to be worn against a body surface (directly or indirectly), or may be associated with other types of flexible substrates, such as sheet-like materials, bandages and other materials that contact the body (directly or indirectly), and may be provided as independently positionable sensor components. Systems and methods for storing, communicating, processing, analyzing and displaying data collected by sensor components for remote monitoring of conditions at body surfaces, or within the body, are also disclosed. Sensors and sensor systems provide substantially real-time feedback relating to current body conditions and may provide notifications or alerts to users, caretakers and/or clinicians, enabling early intervention when conditions indicate intervention is appropriate.

22 Claims, 37 Drawing Sheets

(56) References Cited

U.S. PATENT DOCUMENTS

| | | | |
|---|---|---|---|
| 5,678,448 A * | 10/1997 | Fullen et al. | 73/172 |
| 6,145,551 A | 11/2000 | Jayaraman et al. | |
| 6,155,120 A | 12/2000 | Taylor | |
| 6,174,294 B1 | 1/2001 | Crabb et al. | |
| 6,195,921 B1 * | 3/2001 | Truong | 36/136 |
| 6,216,545 B1 | 4/2001 | Taylor | |
| 6,272,936 B1 * | 8/2001 | Oreper et al. | 73/862.621 |
| 6,315,009 B1 | 11/2001 | Jayaraman et al. | |
| 6,360,597 B1 | 3/2002 | Hubbard, Jr. | |
| 6,381,482 B1 | 4/2002 | Jayaraman et al. | |
| 6,474,367 B1 | 11/2002 | Jayaraman et al. | |
| 6,500,210 B1 * | 12/2002 | Sabolich et al. | 623/24 |
| 6,543,299 B2 | 4/2003 | Taylor | |
| 6,546,813 B2 * | 4/2003 | Hubbard, Jr. | 73/862.041 |
| 6,611,962 B2 | 9/2003 | Redwood et al. | |
| 6,687,523 B1 | 2/2004 | Jayaramen et al. | |
| 6,796,949 B2 | 9/2004 | Horton | |
| 6,918,883 B2 | 7/2005 | Horton et al. | |
| 6,941,775 B2 | 9/2005 | Sharma | |
| 6,970,731 B1 | 11/2005 | Jayaraman et al. | |
| 7,319,895 B2 | 1/2008 | Klefstad-Sillonville et al. | |
| 7,365,031 B2 | 4/2008 | Swallow et al. | |
| 7,395,614 B1 | 7/2008 | Bailey, Sr. et al. | |
| 7,484,408 B2 * | 2/2009 | Healey | 73/149 |
| 7,559,902 B2 | 7/2009 | Ting et al. | |
| 7,726,206 B2 | 6/2010 | Terrafreanca, Jr. et al. | |
| 7,770,473 B2 | 8/2010 | Von Lilienfeld-Toal et al. | |
| 7,997,007 B2 | 8/2011 | Sanabria-Hernandez | |
| 8,060,944 B2 * | 11/2011 | Lueking | 2/22 |
| 8,081,083 B2 * | 12/2011 | Hinterlong | 340/573.4 |
| 8,099,258 B2 | 1/2012 | Alten et al. | |
| 8,109,890 B2 | 2/2012 | Kamiar et al. | |
| 8,116,898 B2 | 2/2012 | Chung et al. | |
| 8,140,143 B2 | 3/2012 | Picard et al. | |
| 8,206,325 B1 | 6/2012 | Najafi et al. | |
| 8,348,841 B2 | 1/2013 | Varadan | |
| 8,352,211 B2 | 1/2013 | Vock et al. | |
| 8,389,862 B2 | 3/2013 | Arora et al. | |
| 8,416,088 B2 * | 4/2013 | Ortega et al. | 340/573.5 |
| 8,443,634 B2 | 5/2013 | Scheffler et al. | |
| 8,583,272 B2 | 11/2013 | Spector | |
| 8,661,915 B2 * | 3/2014 | Taylor | 73/862.044 |
| 8,676,541 B2 * | 3/2014 | Schrock et al. | 702/188 |
| 2003/0224155 A1 | 12/2003 | Orth et al. | |
| 2008/0001735 A1 | 1/2008 | Tran | |
| 2008/0160851 A1 | 7/2008 | Dunn et al. | |
| 2008/0171914 A1 | 7/2008 | Ouwerkerk et al. | |
| 2008/0287832 A1 | 11/2008 | Collins et al. | |
| 2009/0205879 A1 | 8/2009 | Halsey, IV et al. | |
| 2010/0211355 A1 * | 8/2010 | Horst et al. | 702/173 |
| 2011/0004072 A1 | 1/2011 | Fletcher et al. | |
| 2011/0015498 A1 | 1/2011 | Mestrovic et al. | |
| 2011/0054359 A1 | 3/2011 | Sazonov et al. | |
| 2011/0119812 A1 | 5/2011 | Genz et al. | |
| 2011/0263950 A1 | 10/2011 | Larson et al. | |
| 2011/0267196 A1 | 11/2011 | Hu et al. | |
| 2012/0035509 A1 | 2/2012 | Wilson et al. | |
| 2012/0086550 A1 | 4/2012 | LeBlanc et al. | |
| 2012/0109013 A1 | 5/2012 | Everett et al. | |
| 2012/0184878 A1 | 7/2012 | Najafi et al. | |
| 2013/0137943 A1 | 5/2013 | Pinto Rodrigues | |
| 2013/0185003 A1 | 7/2013 | Carbeck et al. | |
| 2013/0211208 A1 | 8/2013 | Varadan et al. | |
| 2013/0281795 A1 | 10/2013 | Varadan | |
| 2013/0281815 A1 | 10/2013 | Varadan | |

FOREIGN PATENT DOCUMENTS

| | | |
|---|---|---|
| EP | 1610677 B1 | 11/2007 |
| EP | 1938749 A2 | 7/2008 |
| GB | 2439750 A | 1/2008 |
| GB | 2443208 A | 4/2008 |
| GB | 2445760 A | 7/2008 |
| JP | 2004132765 A | 4/2004 |
| WO | 2006030405 A1 | 3/2006 |
| WO | 2007137851 A2 | 12/2007 |
| WO | 2012004774 A1 | 1/2012 |
| WO | 2012055029 A1 | 5/2012 |
| WO | 2012073076 A1 | 6/2012 |

OTHER PUBLICATIONS

Andreoni, Giuseppe et al., "A Review of the Intellectual Property Rights in the Field of Wearable Sensors and Systems," International Journal of Computer Research, vol. 18, No. 3/4, pp. 269-285 (2011).

Bucki, M. et al., "The TexiSense >> Smart Sock >> —Textile Pressure Sensor and 3D Real-time Finite Element Model of the Diabetic Foot for a Daily Prevention of Pressure Ulcers," Proceedings of the 14th Annual European Pressure Ulcer Meeting, Oport, Portugal (2011).

NTT Press Releases, "Electrocardiography is achieved simply by wearing a piece of clothing that has textile electrodes combined with conductive polymer," www.ntt.co.jp/news2013/1302e/130212a.html (2013).

Pacelli, M. et al., "Sensing Fabrics for Monitoring Physiological and Biomechanical Variables: E-textile solutions,"Proceedings of the 3rd IEEE-EMBS, International Summer School and Symposium on Medical Devices and Biosensors, MIT, Boston, USA (Sep. 2006).

Rienzo, Di et al., "Textile technology for the vital signs monitoring in telemedicine and extreme environments," IEEE Trans. Inf. Technol. Biomed., vol. 14, No. 3, pp. 711-717; Abstract—www.ncbi.nlm.nih.gov/pubmed/20421189 (2010).

Tekscan, "Tekscan Adds A401 Sensor to Flexiforce Product Line," www.tekscan.com/a401-force-sensor-released (2007).

Texisense "A 100% textile pressure mat" www.texisense.com/capteur.

Texisense "Pressure ulcer prevention in the diabetic foot" www.texisense.com/pieddiabetique.

Torgan, Carol PhD, Self-Tracking Meets Ready-To-Wear: Make Room in Your Closet for Smart Clothes (Nov. 6, 2011).

Winterhalter, C.A. et al., "Wearable Electro-Textiles for Battlefield Awareness," Materials Research Society, Shur, Wilson, Urban, Ed., Warrendale PA, 2003.

Heapsylon LLC, "International Search Report and Written Opinion," Int'l Patent Application No. PCT/US2013/023686, filed Jan. 29, 2013 (May 8, 2013).

* cited by examiner

FIG. 22B (*) Automatic setup of parameters like filter thresholds, signal gain, voltage-to-pressure formula, etc.

FIG. 22J

SENSORS, INTERFACES AND SENSOR SYSTEMS FOR DATA COLLECTION AND INTEGRATED REMOTE MONITORING OF CONDITIONS AT OR NEAR BODY SURFACES

REFERENCE TO EARLIER FILED PROVISIONAL PATENT APPLICATIONS

This application claims priority from U.S. Provisional Patent Application No. 61/592,333 filed Jan. 30, 2012 and from U.S. Provisional Patent Application No. 61/747,877 filed Dec. 31, 2012. The disclosures of the previous provisional applications are incorporated by reference herein in their entirety.

FIELD

The present invention relates generally to sensors, including flexible and stretchable fabric-based pressure sensors, that may be associated with or incorporated in garments intended to be worn against a body surface (directly or indirectly). Sensors may also be associated with or incorporated in sheet-like materials, bandages and other accessories that contact the body (directly or indirectly), and may be provided as independently positionable sensor components. Systems and methods for storing, communicating, processing, analyzing and displaying data collected by sensor components for remote monitoring of conditions at body surfaces, or within the body, are also disclosed. Sensors and sensor systems provide substantially real-time feedback relating to current body conditions and may provide notifications or alerts to users, caretakers and/or clinicians, enabling early intervention when conditions indicate intervention is appropriate.

BACKGROUND

Various types of sensing systems have been incorporated in shoes, insoles, socks and garments for monitoring various physiological parameters for various applications, including recreational, sporting, military, diagnostic and medical applications. Medical applications for sensing pressure, temperature and the like for purposes of monitoring neuropathic and other degenerative conditions with the goal of alerting an individual and/or medical service providers to sensed parameters that may indicate the worsening of a condition, lack of healing, and the like, have been proposed. Footwear-related sensing systems directed to providing sensory data for patients suffering from neuropathy, for gait analysis, rehabilitation assessment, shoe research, design and fitting, orthotic design and fitting, and the like, have been proposed.

Potential causes of peripheral neuropathy include diabetes, alcoholism, uremia, AIDS, tissue injury and nutritional deficiencies. Peripheral neuropathy is one of the most common complications of diabetes and results in wounds, ulcers, etc., which may be undetected and unsensed by the individual. There are 25 million diabetics in the US alone, with a projected population of 500 million diabetics worldwide by 2030. In the presence of neuropathy, diabetic patients often develop ulcers on the sole of the foot in areas of moderate or high pressure and shear, often resulting from walking during normal daily activities. About 70% of diabetics have measurable neuropathy, and every year about 5% of those patients get foot ulcers, and about 1% requires amputations. Foot ulcers are responsible for more hospitalizations than any other complication of diabetes and result in at least $40 billion in direct costs annually.

There is strong evidence that uncomplicated plantar ulcers can be healed in 6-8 weeks, yet current US clinical trials have reported a 76% treatment failure rate at 12 weeks. Many approaches to monitoring diabetic patients for the purpose of preventing ulceration from occurring, or to facilitate healing of existing ulcers, have been proposed, yet little or no improvement in ulceration or its complications has been observed. Off-loading may be an important aspect of ulcer prevention and healing. In "*Practical guidelines on the management and prevention of the diabetic foot*," the authors concluded that mechanical off-loading is the cornerstone of treatment for ulcers with increased biomechanical stress. See, Diabetes Metab Res Rev 2008; 24(Suppl 1): S181-S187. It has been demonstrated that the offloading capacity of custom-made footwear for high-risk patients can be effectively improved and preserved using in-shoe plantar pressure analysis as guidance for footwear modification, which should reduce the risk of pressure-related diabetic foot ulcers. See, e.g., Diabet Med. 2012 December; 29(12):1542-9.

Sensing devices and footwear having sensors incorporated for monitoring pressure and other body parameters have been proposed. These devices have generally not been successful in preventing ulceration or accelerating healing of wounds, in part as a result of poor patient compliance. Notwithstanding the existence of several pressure sensing systems, the incidence of, patient pain and costs associated with diabetic ulcers has not declined. In one aspect, the components and assemblies for collection and analysis of data from sites such as feet and other body surfaces described herein are directed to providing intermittent or continuous monitoring and reporting of body conditions (such as pressure) at body locations for purposes of reducing the incidence and severity of ulcers and other wounds and accelerating the pace and quality of wound healing. In other aspects, sensors, interfaces, systems and materials described herein for collection and analysis of physiological and biomechanical data from sites such as feet and other body parts may be used for a variety of sports-related, military, fitness, diagnostic and therapeutic purposes.

SUMMARY

In one aspect, sensor systems of the present invention comprise one or more sensor(s) mounted to or incorporated in or associated with a substrate material such as a wearable garment, a wearable band, an independently positionable component, or another substrate, such as a flexible and/or pliable sheet material. In one aspect, sensors are capable of sensing a physiological parameter of the underlying skin or tissue, or sensors are capable of sensing force or pressure exerted on or against an underlying skin or tissue. Each sensor is electrically connected, via one or more flexible leads, to a flexible conductive trace mounted to or incorporated in or associated with the substrate, and conductive traces terminate at conductive signal transfer terminals mounted to or incorporated in or associated with the substrate. Sensor systems and sensing devices described herein preferably comprise at least one flexible sensor (or means for sensing), and one or more of the sensor(s), flexible leads, and conductive traces may be stretchable and/or elastic as well as being flexible. In some embodiments, the sensor(s), flexible leads and conductive traces may all comprise flexible, pliable electrically conductive fabric materials. Garments incorporating such sensor systems and sensing devices may be comfortably worn by users under many conditions, providing real time monitoring of conditions at or near body surfaces to the user, a caretaker, and/or clinician.

The signal transfer terminal(s) on the substrate may be matingly received in signal receipt terminals associated with a Dedicated Electronic Device (DED) that is attachable to the substrate and serves as a (temporary or permanent) data collection device. The DED may also (optionally) house batteries or other energy storage devices and serve as a sensor charging device. The DED communicates with one or more external electronic device(s), such as a smartphone, personal computing device/display, host computer, or the like for signal transfer, processing, analysis and display to a user and/or others. In some embodiments, the external electronic device, and/or the DED, communicates with an external, hosted computing system (operated, e.g., at a centralized, hosted facility and/or in the "Cloud") that provides additional data analysis, formulates feedback, notifications, alerts, and the like, that may be displayed to the user, a caretaker, and/or a clinician through one or more computing and/or display devices.

In some embodiments, one or more sensor(s) detect changes in voltage or resistance across a surface area that is associated with force exerted on the sensor, which is related to pressure (as force per unit surface area) and/or shear. In some embodiments, FSR (Force Sensitive Resistor) or piezo-resistive sensors may be used. One type of piezoresistive force sensor that has been used previously in footwear pressure sensing applications, known as the FLEXIFORCE® sensors, can be made in a variety of shapes and sizes, and measure resistance, which is inversely proportional to applied force. These sensors use pressure sensitive inks with silver leads terminating in pins, with the pressure sensitive area and leads sandwiched between polyester film layers. FLEXIFORCE® sensors are available from Tekscan, Inc., 307 West First Street, South Boston, Mass. 02127-1309 USA. Other types of sensors may also be integrated in or associated with various substrate materials (e.g., garments, sheet materials and the like), including sensors providing data relating to temperature, moisture, humidity, stress, strain, heart rate, respiratory rate, blood pressure, blood oxygen saturation, blood flow, local gas content, bacterial content, multi-axis acceleration, positioning (GPS) and the like. A variety of such sensors are known in the art and may be adapted for use in sensing systems described herein.

In some embodiments, pressure sensors and/or associated leads and/or conductive traces incorporated in sensing systems of the present invention comprise non-silicon-based materials such as flexible, conductive "e-textile" fabric material(s). In some embodiments, sensors and/or associated leads and/or conductive traces incorporated in sensing systems of the present invention comprise flexible, conductive fabric materials that are substantially isotropic with respect to their flexibility and/or stretch properties. By "substantially" isotropic, we mean to include materials that have no more than a 15% variation and, in some embodiments, no more than a 10% variation in flexibility and/or stretch properties in any direction, or along any axis of the material. Suitable materials, such as piezoresistive fabric sensors, coated and/or impregnated fabrics, such as metallic coated fabric materials and fabric materials coated or impregnated with other types of conductive formulations, are known in the art and a variety of such fabric sensors may be used. In some embodiments, pressure sensors comprise flexible conductive woven fabric material that is stretchable and/or elastic and/or substantially isotropic with respect to their flexibility and/or stretch properties.

Fabrics comprising a knitted nylon/spandex substrate coated with a conductive formulation are suitable for use, for example, in fabricating biometric pressure sensors and in other applications requiring environmental stability and conformability to irregular configurations. One advantage of using these types of e-textile sensors is that they perform reliably in a wide variety of environments (e.g. under different temperature and moisture conditions), and they're generally flexible, durable, washable, and comfortably worn against the skin. Suitable flexible conductive fabric materials are available, for example, from VTT/Shieldex Trading USA, 4502 Rt-31, Palmyra, N.Y. 14522, from Statex Productions & Vertriebs GmbH, Kleiner Ort 11 28357 Bremen Germany, and from Eeonyx Corp., 750 Belmont Way, Pinole, Calif. 94564.

Techniques for deriving force and/or pressure measurements using e-textile fabric materials are known in the art and various techniques may be suitable. See, e.g., http://www.kobakant.at/DIY/?p=913. Techniques for measuring other parameters using e-textile fabric materials, such as humidity and temperature measurements, are also known and may be used in sensing systems of the present invention. See, e.g., http://www.nano-tera.ch/pdf/posters2012/TWIGS105.pdf. Fabric sensors of the present invention may thus be capable of monitoring various parameters, including force, pressure, humidity, temperature, gas content, and the like, at the site. Additional monitoring capabilities may be available using fabric sensors as innovation in fabric sensors proceeds and as nano-materials and materials incorporating nano-structures are developed and become commercially feasible. Flexible (and optionally stretchable or elastic) conductive fabric sensor(s), leads and/or traces may be mounted to/in/on, or associated with, an underlying substrate such as fabric or sheet material that's non-conductive and flexible. The term "fabric" or "sheet material" as used herein, refers to many types of pliable materials, including traditional fabrics comprising woven or non-woven fibers or strands, as well as fiber reinforced sheet materials, and other types of flexible sheeting materials composed of natural and/or synthetic materials, including flexible plastic sheeting material, pliable thermoplastic, foam and composite materials, screen-like or mesh materials, and the like. The underlying substrate may comprise a sheet material fabricated from flexible fabric material that is stretchy and/or elastic. The sheet material forming the underlying substrate may be substantially isotropic with respect to its flexibility and/or stretch properties. By "substantially" isotropic, we mean to include materials that have no more than a 15% variation and, in some embodiments, no more than a 10% variation in flexibility and/or stretch properties in any direction, or along any axis of the material.

For garment applications, for example, one or more sensor(s) and/or sensing devices may be mounted to (e.g., sewn or otherwise attached or connected or fixed to) an internal surface of a garment for contacting an individual's skin, directly or indirectly, during use, and detecting pressure exerted against an individual's skin, or other parameters sensed at or near a skin surface. In situations where pressure or other parameters are desired to be measured as they impact an outer surface or fabric layer, one or more sensor(s) may be mounted (e.g., sewn or otherwise attached or connected or fixed to) an external surface of a garment. For applications such as bands, bandages and independently positionable sensing components, sensors may likewise be mounted to/in/on, or associated with (e.g., sewn or otherwise attached or connected to or fixed to) an underlying substrate that may be conveniently positioned as desired by the user, a caretaker or clinician. In alternative embodiments, conductive yarns and/or e-textile fabric sensors may be knitted into, sandwiched between substrate layers (as in compression socks) or otherwise incorporated in fabric substrates.

In some embodiments, conductive fabric sensors may be partially or fully enclosed in a flexible barrier material or envelope. Conductive fabrics employed for the sensors, leads and/or traces are generally water resistant and water resistant fabrics are suitably used, without the use of a barrier, for many applications. In cases where the sensor is frequently exposed to body fluids, natural liquids or other solutions (e.g., water, sweat, other bodily fluids) however, the e-properties (e.g., electrical conductivity) of the material can be negatively affected by fluid contact and build up of biological or other debris. To mitigate this condition, a substantially liquid impervious barrier may be provided to protect the sensor(s), leads and/or traces from direct contact with liquids or other materials. In some embodiments, a sandwich approach in which a conductive sensor is enclosed in a substantially liquid impervious barrier may be employed to protect the sensor from contact with liquids and preserve the core resistive features (e-properties) and functions of the sensor(s). Providing a protective barrier covering and/or enclosing the sensor(s) may also be particularly useful in cases when the sensor(s) cannot be exposed directly to an open wound or to a particularly sensitive area of human skin. The barrier may be placed to seal the sensor(s) alone, or the leads and/or traces may be sealed as well. When protected sensing components are used, external surface(s) of the barrier layer(s) may be attached to the underlying substrate (e.g., garment, skin or the like) via adhesive materials or in other ways.

Each sensor is generally associated with two conductive leads, and each of the leads is electrically connected to a conductive trace conveying electrical signals to a signal transfer terminal. Conductive e-textile fabric sensors as previously described may be electrically connected to conductive leads, or may have a flexible fabric lead associated with or incorporated in the fabric sensor footprint. In general, flexible, conductive e-textile leads may comprise conductive fabric materials having high electrical conductivity. Other types of flexible leads, including conductive yarns, fibers, and the like may also be used. The conductive leads are electrically connected to flexible conductive traces, which may comprise a variety of flexible conductive materials, such as a conductive fabric, conductive yarn, or the like. In some embodiments, the conductive traces are stretchable and/or elastic, at least along the longitudinal axis of the conductive trace. In some embodiments, conductive traces comprise a conductive e-textile fabric having high electrical conductivity, such as silver coated e-textile materials, and may be bonded to the underlying substrate material using adhesives, heat bonding or non conductive threads. Suitable e-textile materials are known in the art and are available, for example, from the vendors identified above.

Sensor(s) as described herein and sensor systems, including fabric e-textile pressure sensors and a variety of other types of sensors, with conductive leads and traces, may be associated with a variety of substrates including, without limitation, garments intended to be worn (directly or indirectly) against the skin of an individual, such as a shirt or tunic, underwear, leggings, socks, footies, gloves, caps, bands such as wrist bands, leg bands, torso and back bands, brassieres, and the like. Sensors and sensor systems may additionally be associated with wraps having different sizes and configurations for fitting onto or wrapping around a portion of an individual's body, and with bands, bandages, wound dressing materials, as well as with other types of accessories that contact a user's body surface (directly or indirectly) such as insoles, shoes, boots, belts, straps, and the like. Conductive leads associated with each sensor are electrically connected to conductive traces, as described, which terminate at signal transfer terminals associated with the underlying substrate garment, band, wrap, bandage, or the like.

Each of the conductive traces terminates in a signal transfer terminal that is mounted to/in/on, or associated with, the underlying substrate and can be associated with a mating signal receipt terminal of a dedicated electronic device (DED) having data storage, processing and/or analysis capabilities. In general, conductive traces and terminals are arranged in a predetermined arrangement that corresponds to the arrangement of signal receipt terminals in the DED. Many different types of signal transfer and receipt terminals are known and may be used in this application. In one exemplary embodiment, signal transfer and receipt terminals may be mounted in cooperating fixtures for sliding engagement of the terminals. In another embodiment, signal transfer terminals may be provided as conductive fixtures that are electrically connected to the conductive trace (and thereby to a corresponding sensor) and detachably connectable to a mating conductive fixture located on the DED. The mating terminals may comprise mechanically mating, electrically conductive members such as snaps or other types of fasteners providing secure mechanical mating and high integrity, high reliability transfer of signals and/or data. In some embodiments, easy and secure mating of the terminals may be enhanced using magnetic mechanisms or other types of mechanisms that help users to properly connect/disconnect the mating terminals with minimal effort. For example, the mechanism may allow an overweight diabetic patient to reach down to his own legs or feet and easily snap or unsnap the DED to/from the wearable device without excessive effort.

The DED, in addition to having data recording, processing and/or analysis capabilities, may incorporate an energy source such as a battery providing energy for data recording, processing and/or analysis, as well as providing energy for operation of one or more of the sensor(s). The energy source is preferably a rechargeable and/or replaceable battery source. The DED generally provides a lightweight and water-tight enclosure for the data collection and processing electronics and (optional) energy source and provides receiving terminals that mate with the transfer terminals connected to the sensor(s) for conveying data from the sensors to the dedicated electronic device.

Dedicated electronic devices having signal receipt terminals that mate with the signal transfer terminals associated with the substrate may take a variety of form factors, depending on the form factor of the underlying sensing substrate and/or the conditions and location of the device during use. When sensors are incorporated in a sock-like form factor for monitoring conditions sensed at the foot, for example, the signal transfer terminals may be arranged in proximity to one another in an ankle region of the sock, and the DED may have the curved form factor of a band that extends partially around the ankle or lower leg and attaches to the underlying signal transfer terminals and sock substrate along a front and/or side portion of the user's ankle or lower leg. When sensors are incorporated in a wrap or band, the signal transfer terminals may be arranged at or near an exposed end of the wrap or band following its application to an underlying anatomical structure or body surface, and the DED may be provided as a band or a tab or a dongle-like or capsule-like device having aligned signal receipt terminals. The DED may be provided as a substantially flexible or a substantially rigid component, depending upon the application, and it may take a variety of forms.

The DED preferably communicates with and transfers data to one or more external computing and/or display system(s), such as a smartphone, computer, tablet computer, dedicated computing device, medical records system or the like, using wired and/or wireless data communication means and protocols. The DED and/or an external computing and/or display system may, in turn, communicate with a centralized host computing system (located, e.g., in the Cloud), where further data processing and analysis takes place. Substantially real-time feedback, including data displays, notifications, alerts and the like, may be provided to the user, caretaker and/or clinician according to user, caretaker and/or clinician preferences.

In some embodiments, the DED may store the data temporarily to a local memory, and periodically transfer the data (e.g., in batches) to the above mentioned external computing and/or display system(s). Offline processing and feedback, including data displays, notifications and the like may be provided to the user, caretaker, and/or clinician according to user, caretaker and/or clinician preferences.

In operation, an authentication routine and/or user identification system matches the DED and associated sensing system (e.g., the collection of sensor(s) associated with an underlying substrate) with the user, caretaker and/or clinician, and may link user information or data from other sources to a software- and/or firmware-implemented system residing on the external computing system. The external computing device may itself communicate with a centralized host computing system or facility where data is stored, processed, analyzed, and the like, and where output, communications, instructions, commands, and the like may be formulated for delivery back to the user, caretaker and/or clinician through the external computing device and/or the DED.

Calibration routines may be provided to ensure that the DED and connected related sensor system are properly configured to work optimally for the specific user. Configuration and setup routines may be provided to guide the user (or caretaker or medical professional) to input user information or data to facilitate data collection, and various protocols, routines, data analysis and/or display characteristics, and the like, may be selected by the user (or caretaker or medical professional) to provide data collection and analysis that is targeted to specific users. Specific examples are provided below. Notification and alarm systems may be provided, and selectively enabled, to provide messages, warnings, alarms, and the like to the user, and/or to caretakers and/or medical providers, substantially in real-time, based on sensed data.

BRIEF DESCRIPTION OF THE DRAWINGS

FIG. 12A shows a schematic exploded diagram illustrating exemplary components of the male connector; FIG. 12B shows a schematic exploded diagram illustrating exemplary components of the female connector.

FIG. 18A shows one face of the assembled sensor system and FIG. 18B shows the opposite face of the assembled sensor system.

FIGS. 22A-22L illustrate exemplary device set ups, calibration and monitoring criteria input and routines, along with an exemplary clinician dashboard, a graphical representation of patient offloading data, and an exemplary sample of acquired pressure data. FIG. 22A shows exemplary setup and calibration steps; FIG. 22B shows an exemplary patient data input routine; FIG. 22C shows an exemplary device setup routine; FIG. 22D shows an exemplary device setup routine; FIG. 22E shows another exemplary device setup routine; FIG. 22F shows another exemplary device setup routine; FIG. 22G shows an exemplary monitoring routine setup; FIG. 22H shows another exemplary monitoring routine setup; FIG. 22I shows an exemplary user calibration routine; FIG. 22J shows an exemplary clinician dashboard presenting patient status information for a plurality of patients using a sensing device of the present invention; FIG. 22K shows an exemplary patient offloading data display; and FIG. 22L shows exemplary pressure data collected using an exemplary sensing system of the present invention.

Figure 1:
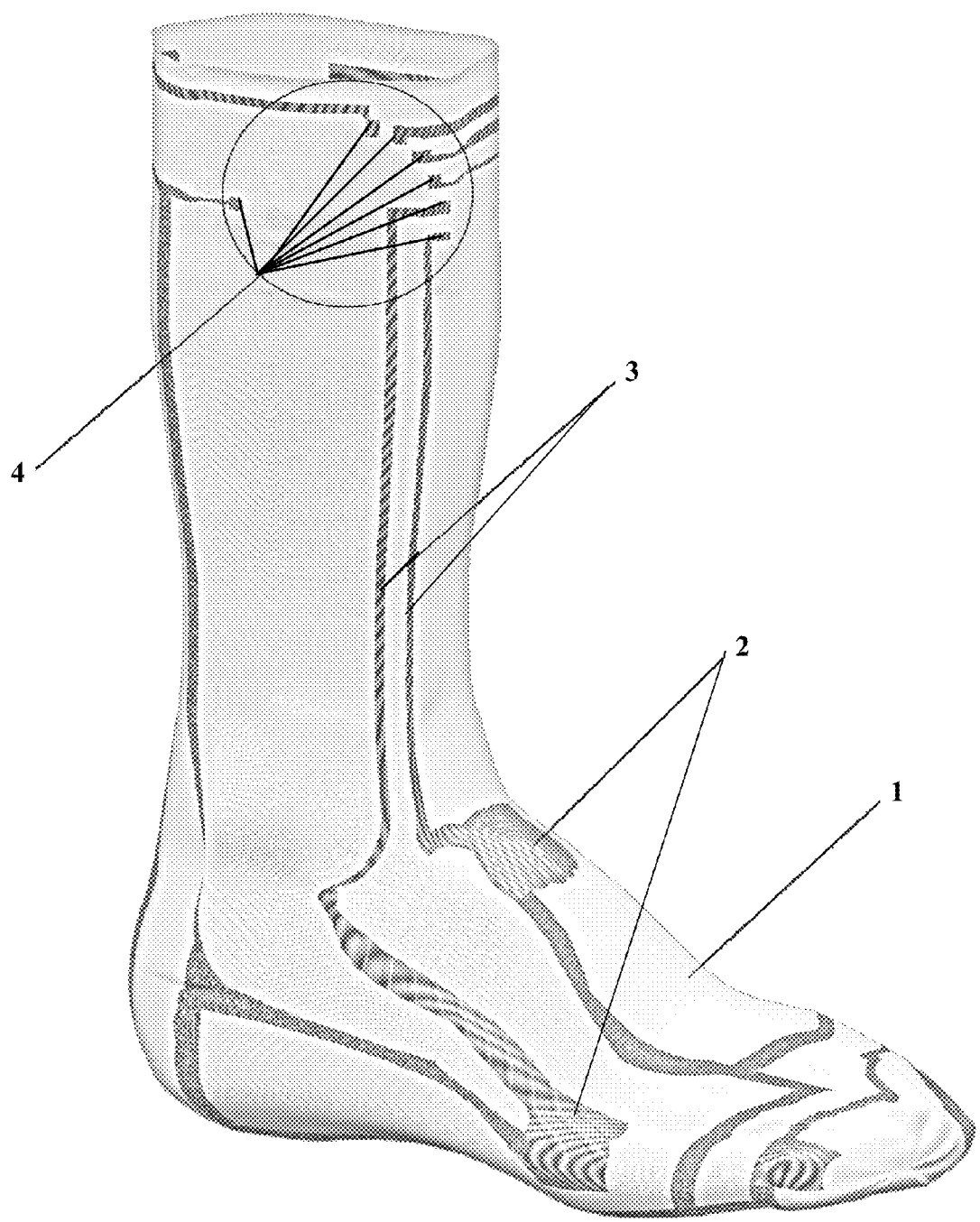
FIG. 1 shows an exemplary sensing device having a sock form factor and having one or more sensor patches electrically connected to one or more terminals by means of conductive pathways.
Figure 2:
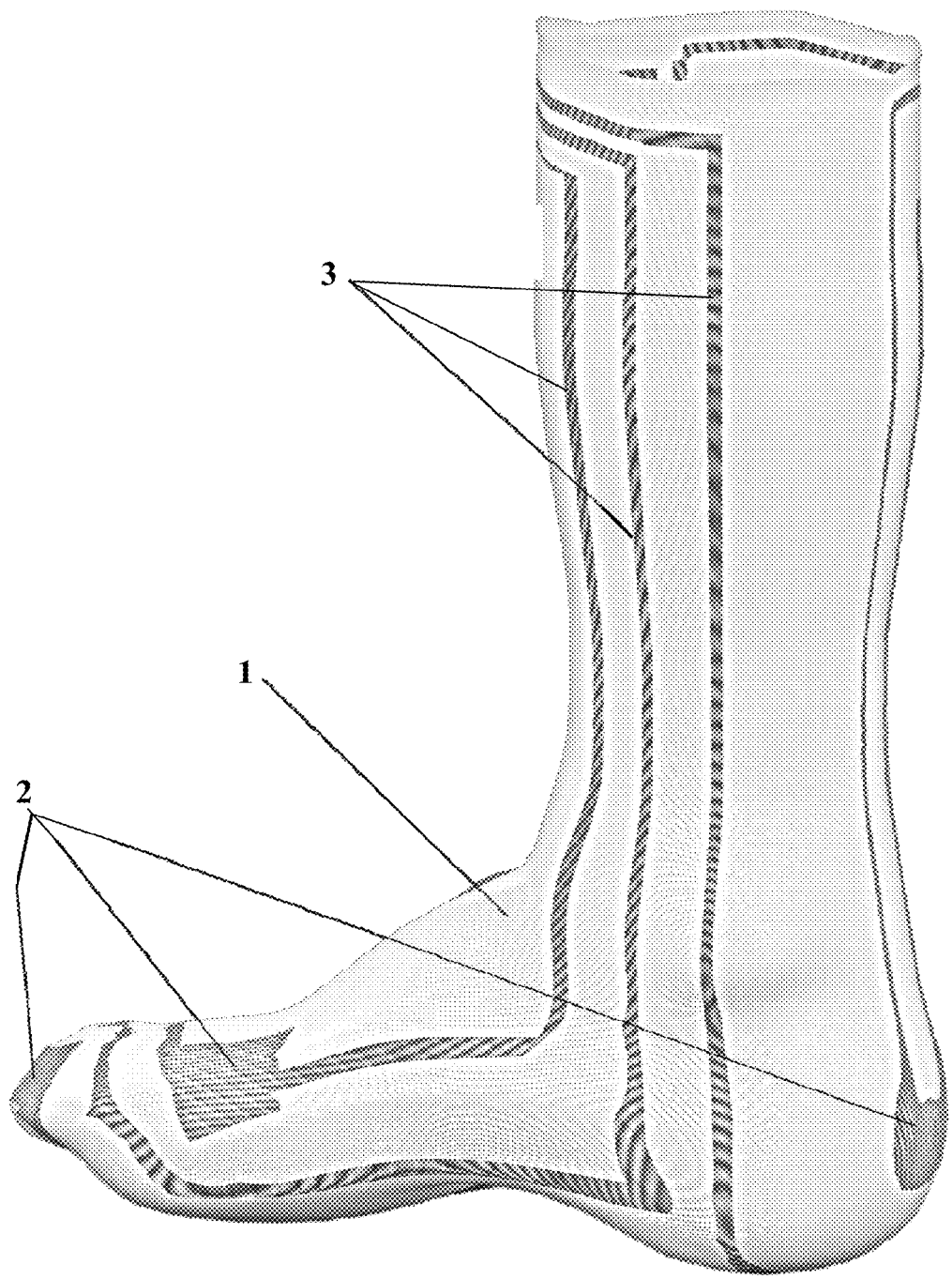
FIG. 2 shows another exemplary sensing device similar to that shown in FIG. 1 and having a different arrangement of sensor patches electrically connected to terminals by means of conductive pathways.
Figure 3:
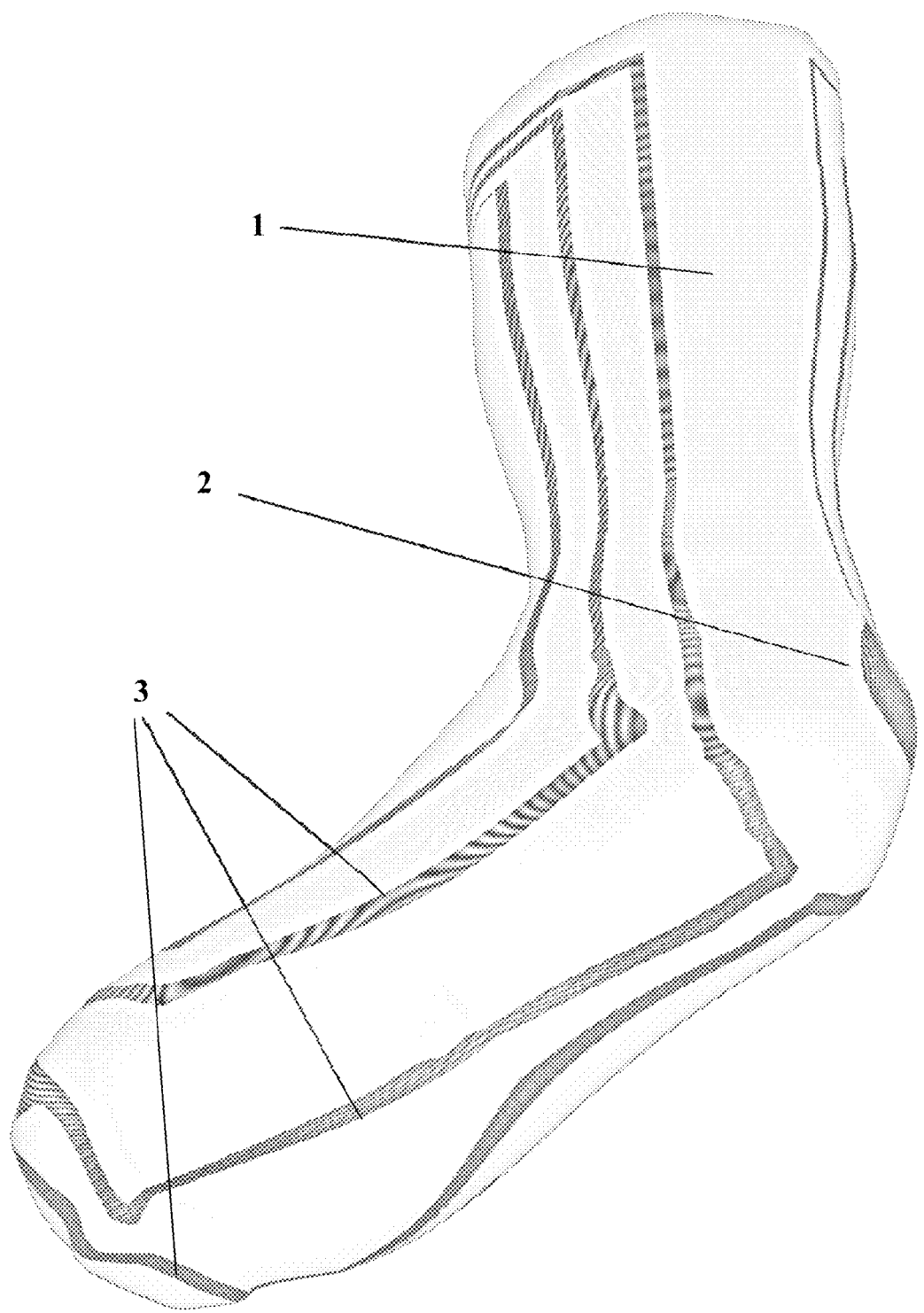
FIG. 3 shows another view of an exemplary sensing device similar to that shown in FIGS. 1 and 2.

It will be understood that the appended drawings are not necessarily to scale, and that they present simplified, schematic views of many aspects of systems and components of the present invention. Specific design features, including dimensions, orientations, locations and configurations of various illustrated components may be modified, for example, for use in various intended applications and environments.

DETAILED DESCRIPTION OF EXEMPLARY EMBODIMENTS

Sensors and Sensor Systems Used in a Sock-Like Form Factor

In one embodiment, systems incorporating sensors, leads, traces and terminals may be mounted to and/or incorporated in or associated with a garment having a sock-like form factor. One version of this embodiment is illustrated in FIGS. 1-5. In general, a substrate material in the form of a sock may be equipped with one or more sensors, leads, traces and connectors that provide signals and/or data to a dedicated (and preferably detachable) electronic device that gathers data from each sensor and communicates to an external computer and/or mobile device. Sensors used in footwear and sock applications typically include pressure sensors capable of detecting levels of pressure (and/or force and/or shear) at one or more areas of the foot and may include other types of sensors, including temperature, accelerometers, heart rate monitors and/or moisture sensors, and the like. Based on the detected pressure, force and/or shear at one or more areas of the foot, and trends in those parameters over one or more monitoring period(s), conclusions relating to the lack of proper offloading and related conditions of the underlying skin or tissue, healing progression (or lack of healing), discomfort, extent and seriousness of injury, and the like, may be drawn and may be communicated to the user, caretaker and/or clinician, essentially in real time. In addition, notifications, alerts, recommended actions, and the like may also be communicated to the user, caretaker and/or clinician based on the data analysis, essentially in real time. These systems are suitable for use in medical and patient adherence monitoring applications, diabetic (and other) foot monitoring, sports and fitness applications, footwear fitting applications, military applications, etc.

One embodiment of a sensor system embodied in a sock-like form factor is illustrated in FIGS. 1-5. In this embodiment, a flexible and preferably stretchable fabric substrate in the form of a sock 1 has one or more sensors, shown as sensor patches 2, optionally including one or more pressure sensors constructed from flexible and conductive fabric as disclosed herein. Each of the sensor patches 2 has leads and conductive traces or threads 3, each terminating in a conductive signal transfer terminal 4. The sensor patches 2 and conductive traces or threads 3 may be woven into the fabric forming the sock, or may be applied to a surface of the fabric forming the sock. In one embodiment, e-textile fabric pressure sensors are applied to an internal surface of the fabric that contacts a user's skin (directly or indirectly) when the sock is worn. Additional fabric sensors may be used in connection with the sock, and other types of sensors, including heat sensors (e.g., thermocouples), moisture sensors, and the like, may also be incorporated in the sock with leads and traces terminating in additional signal transfer terminals. In general, the conductive traces may be applied to an internal or external surface of the underlying fabric substrate, and the terminals preferably have a conductive transfer interface accessible to the external surface of the fabric substrate. In the embodiment illustrated in FIGS. 1-5, the signal transfer terminals 4 are positioned in proximity to the top of the sock, although it will be appreciated they may be positioned elsewhere.

Figure 4:
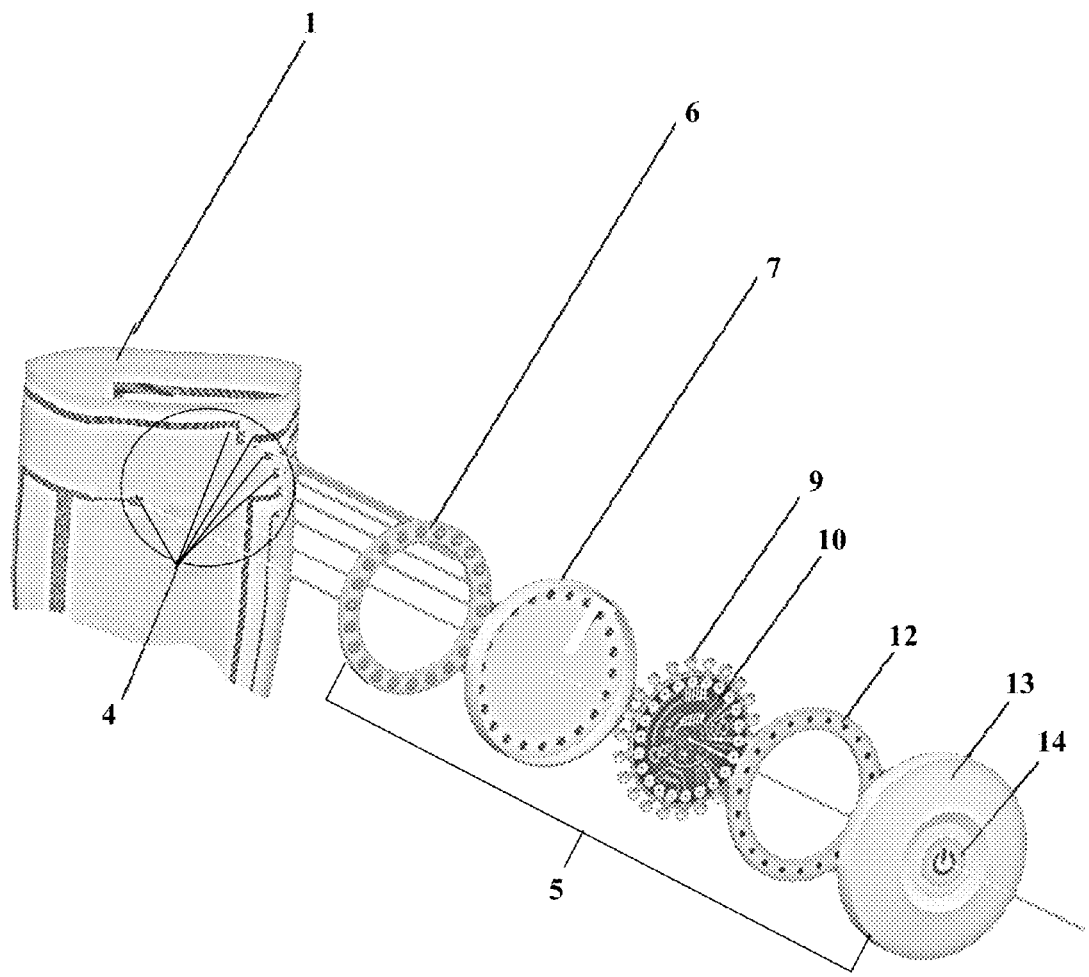
FIG. 4 shows a view of terminals of the sensing device and an exploded view of a detachable dedicated electronic device that, when attached to terminals on the sock, captures and optionally processes, stores and/or analyzes sensed signals or data.
Figure 5:
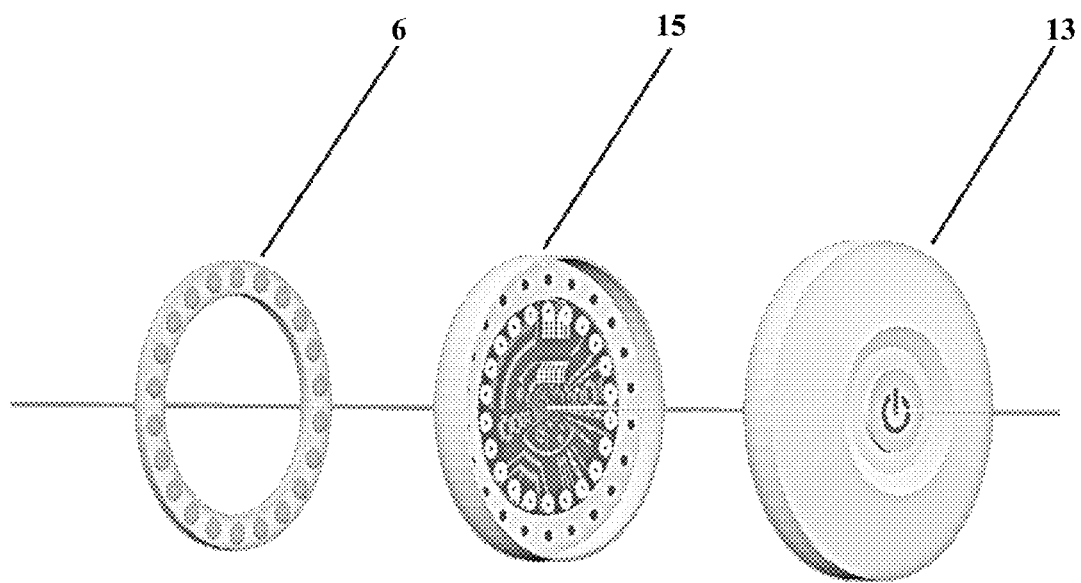
FIG. 5 shows an enlarged, exploded view of an exemplary detachable electronic device similar to that shown in FIG. 4.

The signal transfer terminals 4 that connect to the sensor(s) in the sock are connectible to mating signal receiving terminals of a detachable electronic device (DED). Simplified diagrams illustrating exemplary DEDs are shown in FIGS. 4 and 5. Detachable electronic device 5 receives signals from each of the signal transfer terminals, and thus collects data from each of the sensors. As shown in FIG. 4, the DED may comprise mechanical interface(s) 6 for attaching the DED to terminals 4 located on the sock (or another sensing device); a housing component 7 protecting internal DED components and providing signal transfer from the sensing device (e.g., terminals on the sock) to internal DED components; electronic and communications components 10 and conductive terminals 9 receiving signals from terminals 4 in the sock sensing device; a mating ring 12, and an external housing lid 13 having a power button 14 for activating the DED. An alternative, simplified DED is shown in FIG. 5, comprising mechanical interface(s) 6 for attaching the DED to terminals 4 located on the sock (or another sensing device); an integrated component 15 providing a housing, electronic and communications components, and an external housing lid 13. It will be appreciated that many other types and styles of DEDs may be provided for interfacing with and downloading signals and/or data from the underlying sock sensing device.

Figure 12A:
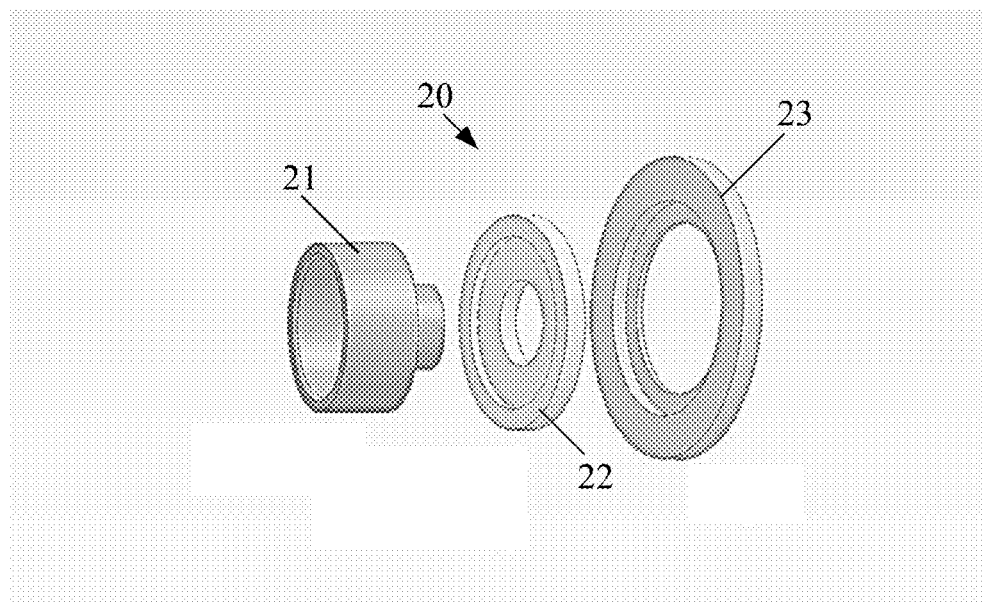
FIGS. 12A and 12B show a schematic diagrams illustrating one embodiment of mating mechanical and magnetic fasteners providing a mechanical and electrical connection between the dedicated electronic component and the signal transmit terminals, via mating magnetic snaps.
Figure 12B:
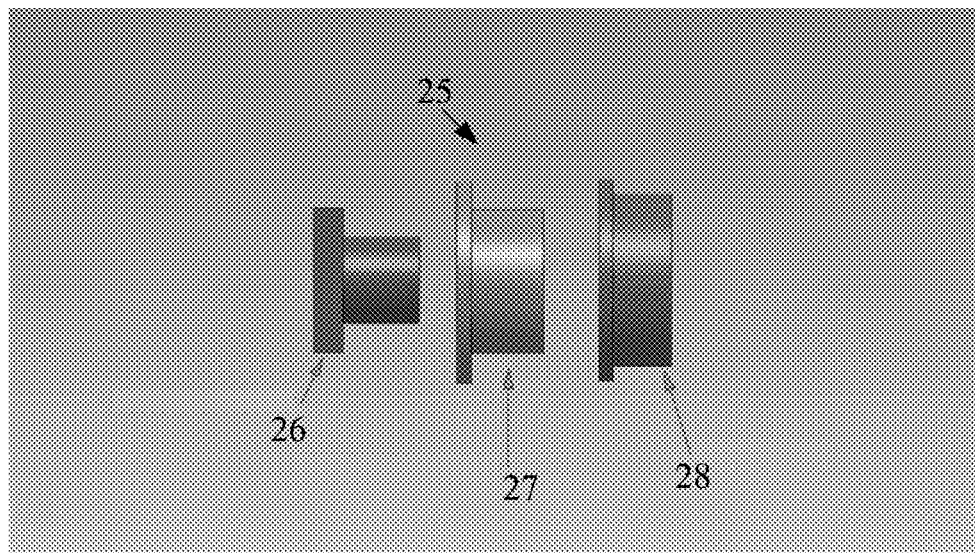

In one embodiment, mechanically mating snaps are used as terminal interfaces and operated as mechanical switches that are switched on and off abruptly by an external driving force from one switch position (attached) to a second position (detached). In another embodiment, conductive, magnetic snap switches are used as mating terminals for transferring signals and/or data from the sock to the DED. FIGS. 12A and 12B show one specific design of such snaps: an external magnetic ring may be used on the male (DED) snap to attract and maintain solid connection with a magnetic component of a female portion of the snap located on the underlying substrate. In this exemplary embodiment, properties of the magnetic field may be used to create snaps that can only connect in one orientation: in this way, the user is guided to properly connect the DED to the sensor system(s) associated with the underlying substrate. Circuitry in the DED may provide the ability to automatically turn the data collection on and off, for example, based on the presence of the magnetic connection between the DED and the sensor system. It will be appreciated that many other types of mechanical and non-mechanical interfaces may be used to attach and detach the DED from the signal transfer terminals, and to transfer signals and/or data from the sensing system to the DED.

Circuitry in the DED may be provided for reading the sensor signals; firmware may be provided for processing signal data, applying post processing algorithms and formatting the data for communication to an external computing and/or display device. The DED may incorporate firmware and/or software components for collecting, filtering, processing, analyzing data, or the like. In one embodiment, the DED hosts firmware subroutines that apply at least some of the following: low pass filtering algorithms to reduce incoming signal noise; pull up resistors logic to avoid shorting of the device and additional noise filtering.

In one embodiment, the DED may be physically attached to the sensing substrate (e.g., sock) for data collection and then detached from the sensor terminals and physically mounted (e.g., through a USB or another wired connection), to an external computing and/or display device such as a phone, personal computing device, computer, or the like to download data. In other embodiments, the DED preferably has wireless communication capability (e.g., using Bluetooth, WiFi, or another wireless standard) and transmits signals and/or data to a computing and/or display device wirelessly. The DED is thus connected through a communication system to an external electronic device having computing and/or display capabilities. The external computing and/or display device generally hosts client firmware and/or software and processing firmware and/or software for processing, analyzing, communicating and/or displaying data. It will be appreciated that the division of functions and processing, such as data processing, analysis, communications and display functions as between the DED and the external computing and/or display device may vary depending on many factors and is, to at least some extent, discretionary.

In some embodiments, client software and communications systems are hosted on the external computing device (e.g., a computer or a mobile device such as a tablet or smartphone), and provide feedback to and interact with the user, communicating through an Internet connection via web services, to push collected data and retrieve processed data from the service and display (or otherwise communicate) it to the user. The client software may comprise a set of applications that can run on multiple platforms (not limited to personal computers, tablets, smartphones) and sub-components (diagnostics, troubleshooting, data collecting, snap and match, shopping) to deliver a rich and complete user experience. The experience can be also delivered through an Internet browser.

For some applications, server software components that apply crowdsourcing logic and/or machine learning technologies may be implemented to identify, profile, and cluster user data. The data may be stored in a database and may be continuously or intermittently updated with incoming user supplied and/or sensor supplied data. An optional software component that provides image and pattern recognition capabilities may also be implemented. This feature may allow a user to input data (e.g. images, external data accessed from databases, etc.) without entering any text input.

While this specific example of sensor systems has been described with reference to a sock form factor, it will be appreciated that e-textile fabric sensors may be used with (and/or applied to) other types of wearable garments (e.g., underwear, t-shirts, trousers, tights, leggings, hats, gloves, bands, and the like), and dedicated electronic devices having different configurations may be designed to interface with a variety of sensor systems embodied in different types of garments. The type of sensor(s), garment(s), placement of sensor(s), user identification, and the like, may be input during an authentication and initial device calibration set up protocol.

Figure 6A:
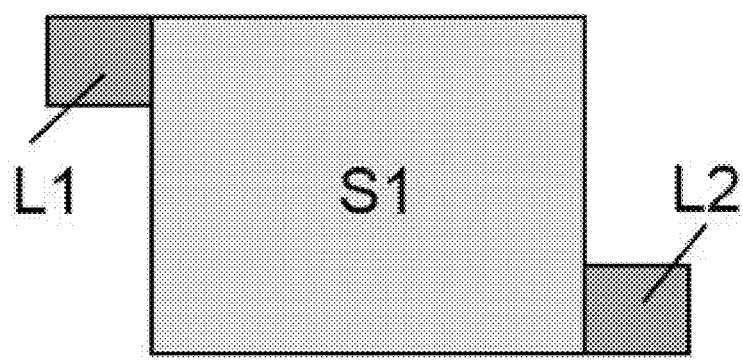
FIGS. 6A and 6B show schematic illustrations of exemplary sensors having leads provided in different configurations.
Figure 6B:
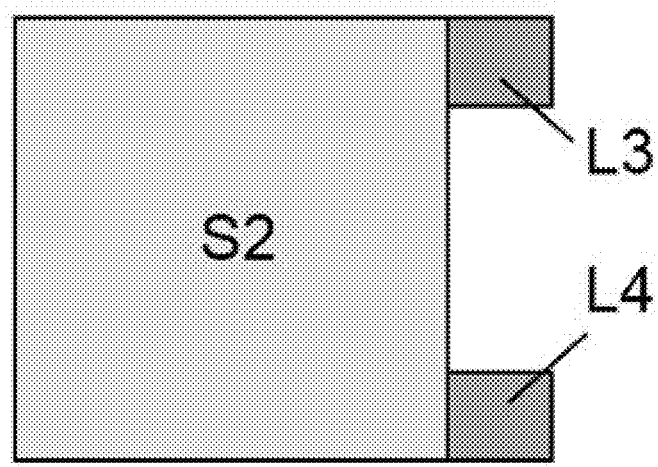

Another exemplary embodiment of a sensor system using e-textile fabric sensors in a sock form factor is shown in FIGS. 6A-13. FIG. 6A shows an exemplary fabric sensor S with leads L1 and L2. In this example, sensor S1 comprises a rectangular piece of e-textile conductive fabric, and conductive leads L1 and L2 are positioned on opposite sides of sensor S1. Conductive leads L1 and L2 are shown as integral extensions, or pieces, of the same conductive fabric of sensor S1, but alternative types of leads may also be used. FIG. 6B shows a similar fabric sensor S2 having integral leads L3, L4 extending from a common side of the sensor. It will be appreciated that although rectangular sensors are illustrated, fabric sensors having a variety of sizes and configurations may be provided. Conductive leads having the same properties as the sensors may be used, or other types of conductive leads may be employed. It will also be appreciated that the arrangement of leads with respect to sensor(s) may vary, depending on the properties, size and configuration of the sensor and lead components.

Figure 7:
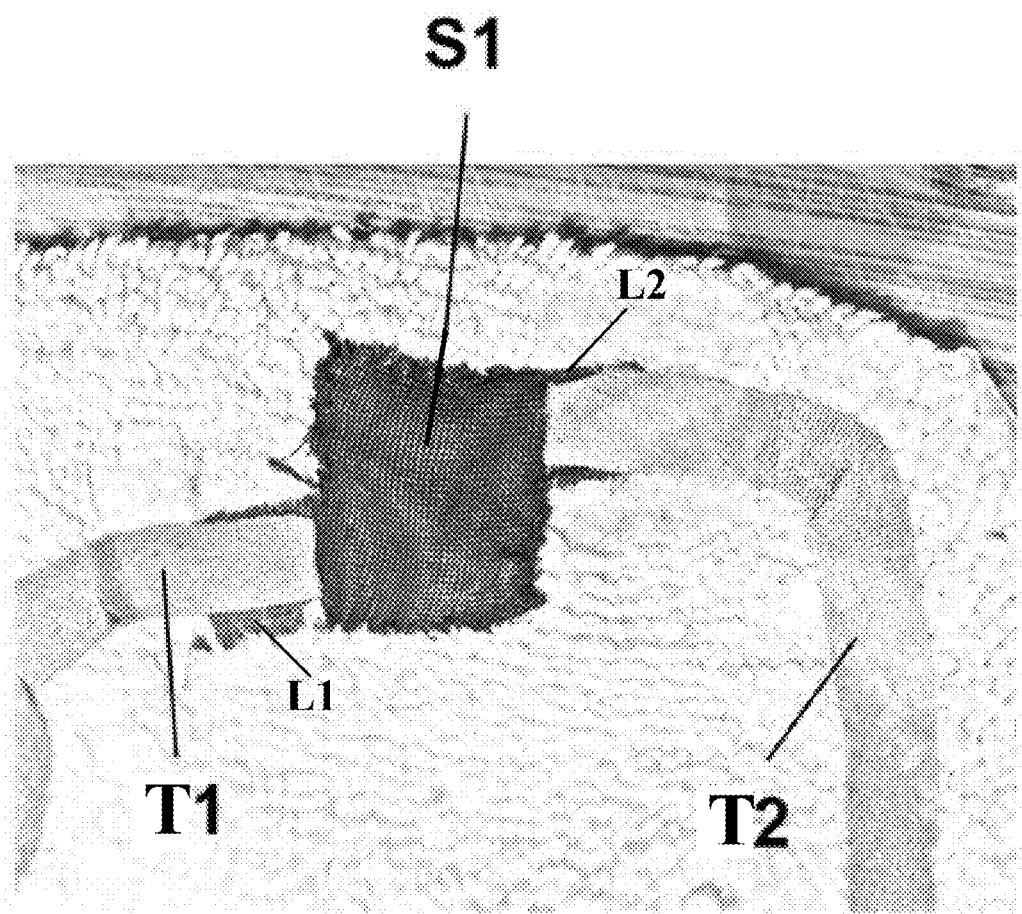
FIG. 7 shows an image illustrating a sensor of the type illustrated in FIG. 6A mounted on a fabric substrate, with each of the leads connected to a conductive trace.

E-textile fabric sensors are mounted to, or associated with, the underlying fabric substrate (e.g., a stretchable, knit fabric) in a variety of ways, including sewing, adhesive bonding, thermal bonding, and the like. FIG. 7 shows an e-textile fabric sensor S1 having the configuration shown in FIG. 6A attached to the inside of a stretchable, knit sock. Sensor leads L1 and L2 are sewn or bonded to the underlying sock, and conductive traces T1 and T2 are mounted and electrically connected to leads L1 and L2, as shown. In this embodiment, conductive traces T1 and T2 are fabricated from e-textile fabric materials having different properties from the materials of the sensor S1 and leads L1 and L2.

Figure 8:
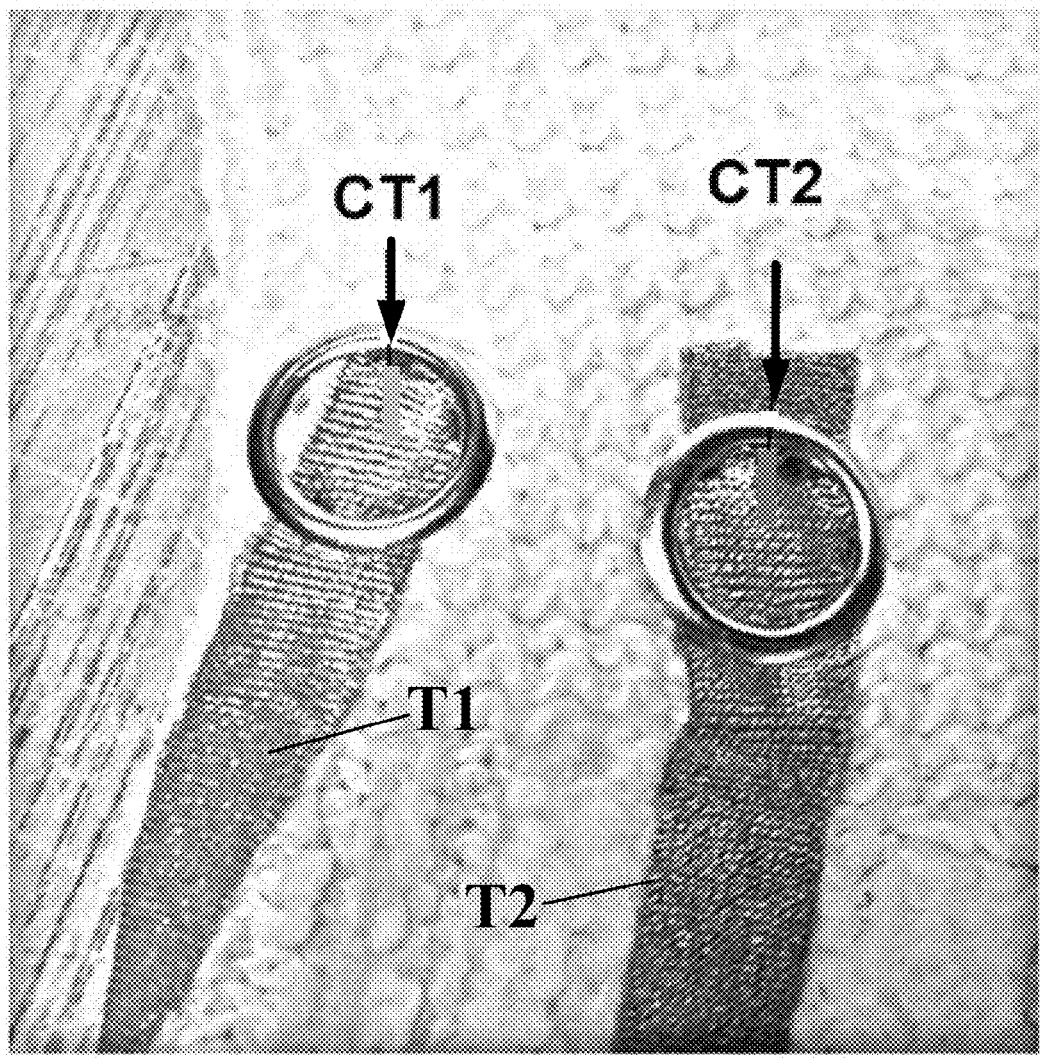
FIG. 8 shows an image illustrating two exemplary conductive traces mounted on an internal surface of a fabric substrate in a sock-like form factor, terminating in conductive signal transmit terminals that penetrate the fabric substrate.
Figure 9:
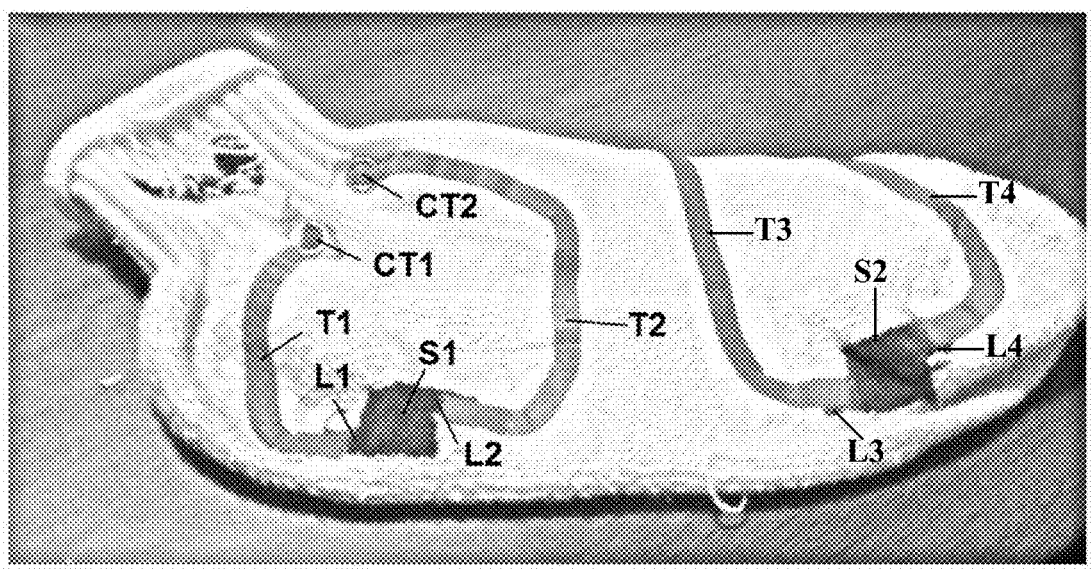
FIG. 9 shows an image illustrating two exemplary sensors of the type illustrated in FIG. 6A mounted on a fabric substrate, with each of the leads connected to a conductive trace and each of the traces terminating in a conductive signal transmit terminal.
Figure 10:
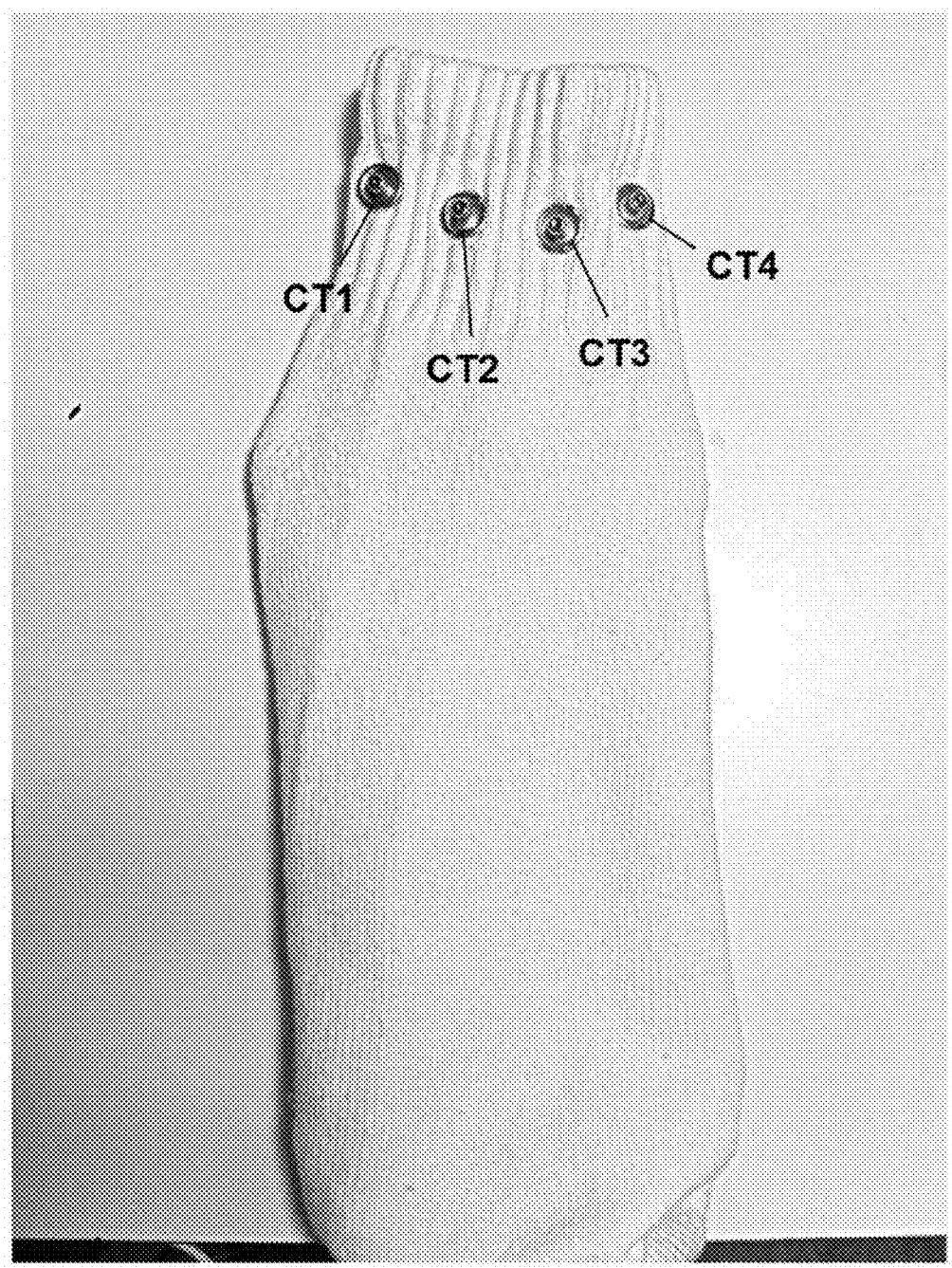
FIG. 10 shows an image illustrating the external surface of a fabric substrate in a sock-like form factor, showing multiple conductive terminals for mating with terminals of an intermediate device.

The conductive traces T1, T2 terminate in conductive terminals CT1, CT2, as shown in FIGS. 8-10. In the embodiment illustrated, conductive terminals CT1, CT2 are provided as conductive mechanical snaps, illustrated in FIG. 8, that penetrate the substrate sock material from the interior to the exterior surface of the sock. The interior of the sock having the sensor/lead/trace/terminal arrangement is illustrated in FIG. 9. Multiple fabric sensors may be implemented, resulting in multiple conductive terminals communicating data collected from multiple sensors located in different areas of the foot. It will be appreciated that other types of sensors may be integrated in this sock format sensing device (and in other formats of sensing devices), and that additional conductive terminals may be provided for transmission of signals and/or data from other types of sensors. The exterior of the sock having signal transfer terminals CT1, CT2 corresponding to a first sensor, and signal transfer terminals CT3 and CT4 corresponding to a second sensor, is illustrated in FIG. 10. In this embodiment, the signal transfer terminals are aligned along a upper circumference of the sock, shown in this embodiment as an anklet.

One embodiment of a signal transfer and signal receipt terminal configuration that detachably mates, mechanically and magnetically, is shown in FIGS. 12A and 12B. This is a mechanical two-part snap device having mating male (FIG. 12A) and female (FIG. 12B) connector components, as shown. The male connector 20 comprises a central conductive pin element 21 surrounded by a non-conductive ring member 22 and having a magnetic perimeter portion 23. The female connector 25 comprises a central conductive pin receiving element 26 and contact that is electrically connected to the conductive area of the male connector when the connector portions are mechanically and/or magnetically connected to one another. Female connector 25 also comprises a non-conductive collar 27 and a magnetic collar 28 sized and configured to mate with corresponding components of the male connector. The components illustrated in FIGS. 12A and 12B are shown in an exploded view; when assembled, the connector components nest to provide compact, highly functional connectors. The polarity of magnetic components 23, 28 may be arranged to provide male and female connectors that are connectable only when magnetically aligned in a predetermined orientation, which may facilitate user connection of the mating terminals. Although this exemplary mating terminal configuration is illustrated having a round configuration, it will be appreciated that other configurations, including oval, linear, polygonal, and the like, may be used.

Figure 11A:
FIGS. 11A and 11B show images illustrating dedicated electronic component for connecting to signal transmit terminals having a curved form factor for mounting at an ankle or lower leg portion of a user.
Figure 11B:
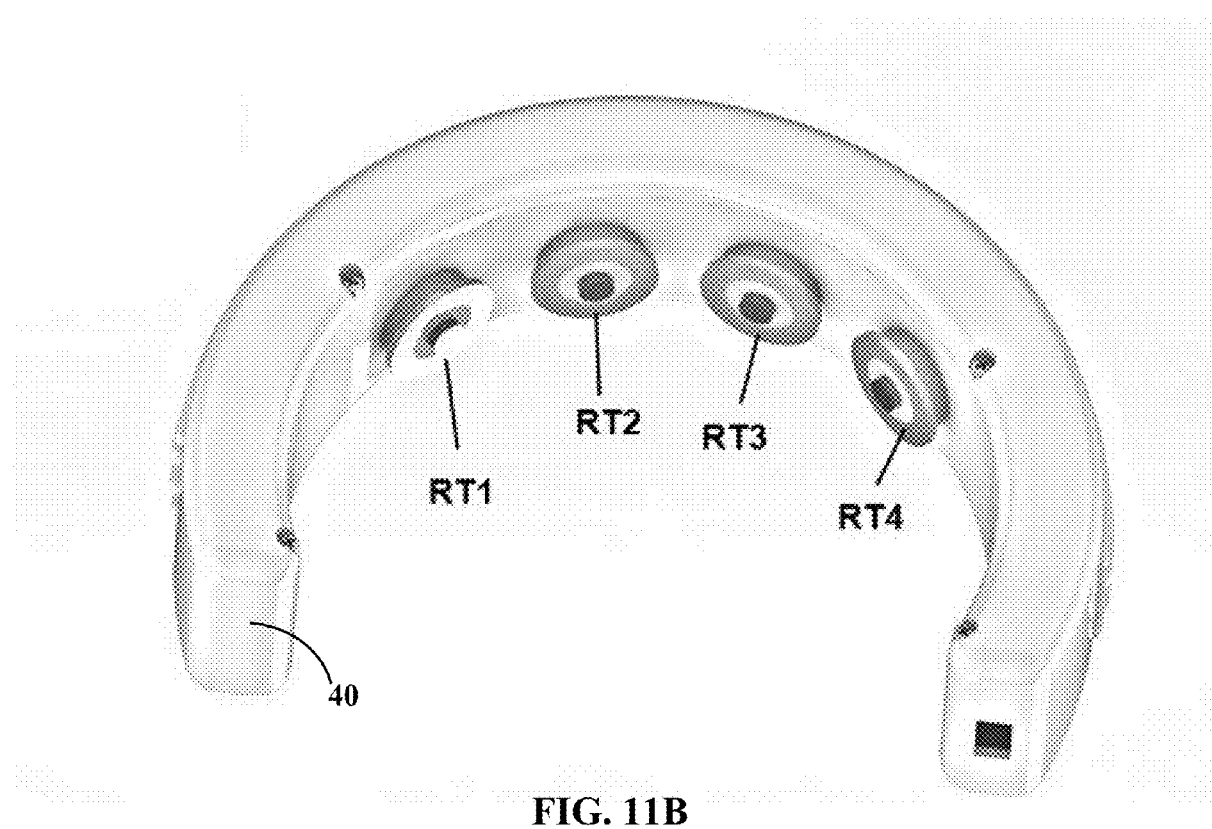
Figure 13:
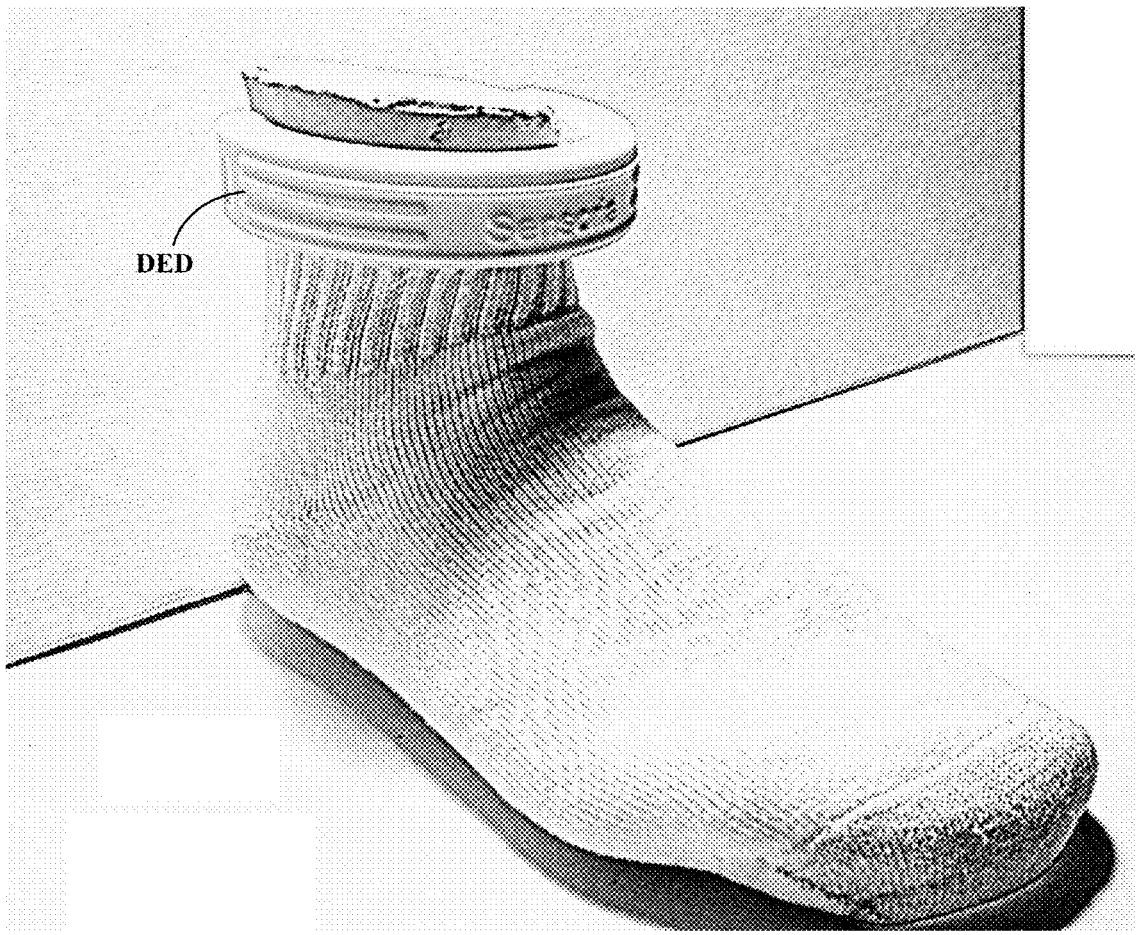
FIG. 13 shows an image illustrating a sensor-activated device of the type shown in FIGS. 7-10 having a sock-like form factor in place on a user's foot, with an intermediate device having an anklet-like form factor as shown in FIGS. 11A and 11B connected to the external terminals for data collection and, optionally, analysis.

FIGS. 11A and 11B illustrate one exemplary embodiment of a dedicated electronic device (DED) 40 having signal receipt terminals RT1, RT2, RT3, RT4 that mate mechanically with conductive terminals such as CT1-CT4 to provide signal and/or data transfer from the sensor/lead/traces associated with the sock substrate to the DED. DED 40, as illustrated in FIGS. 11A and 11B, comprises a curved housing or case enclosing an interior space containing processing, memory and/or communications components. In this embodiment, DED 40 may be installed on the exterior of a sock in the ankle or lower leg area of the user, as illustrated in FIG. 13. DED 40 preferably provides a protective and watertight housing or case protecting the electronic components provided within the housing. The housing may be provided as a substantially rigid or a substantially flexible component and a variety of DED form factors may be provided, depending on the type and arrangement of underlying substrate and signal transfer terminals.

Figure 14:
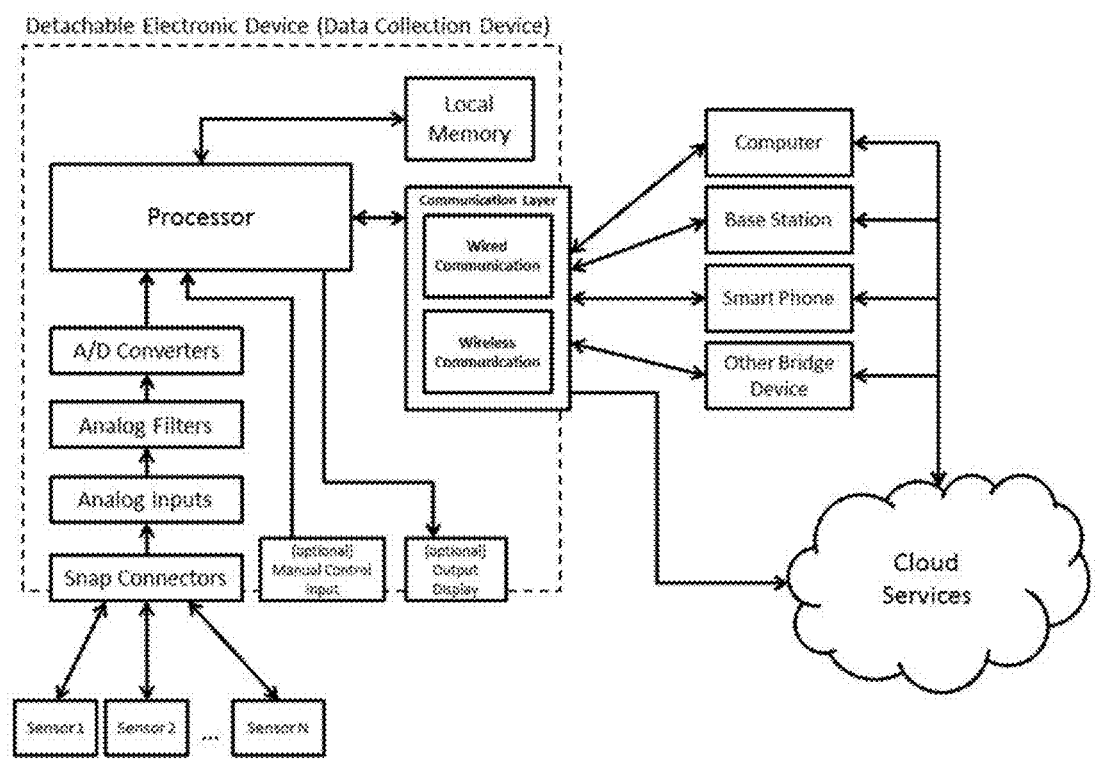
FIG. 14 shows a block diagram illustrating basic components of an exemplary data collection device and illustrating its interface with sensors provided in a substrate, an external computing device, and a centralized host system maintained, for example, in the Cloud.

The DED incorporates processing, memory and/or communications functionalities within the housing. A schematic diagram illustrating exemplary DED components and interfaces is shown in FIG. 14. The DED has signal receipt terminals (shown as "snap connectors") that feed analog input signals to appropriate processing means, such as analog filters, A/D converters, and to a processing component. Optional manual control input(s) and one or more optional output display(s) may be provided in or on the DED, as shown. Local memory may also be provided, and means for communicating signals and/or data externally via wired or wireless protocols may be provided, as shown. Signals and/or data is communicated from the DED to an external computing facility or device, such as a computer, base station, smartphone, or another bridge device, and/or to a centralized, hosted facility in a remote location, such as in the Cloud or at a centralized data processing and analysis facility. Following data analysis in accordance with predetermined and/or pre-programmed instructions, data output, analysis, notifications, alerts, and the like are communicated from the centralized hosted facility to the bridge device, and/or the DED, as shown. It will be appreciated that this is one exemplary data flow scheme, and that many other work flows may be advantageously used in connection with sensing systems of the present invention.

Although these specific embodiments have been illustrated and described with reference to the wearable substrate having a sock form factor, it will be appreciated that the sensors, leads, traces and terminals, as well as different types of DEDs may be adapted for use in other types of garment and non-garment applications. Similar types of flexible e-textile sensors may be applied to or associated with a wide variety of non-conductive underlying flexible substrate materials, including woven and non-woven materials, and incorporated in a variety of sensor systems. Additional exemplary systems are described below, and are non-limiting.

Wrap, Band and Sheet Sensor Applications

Figure 15:
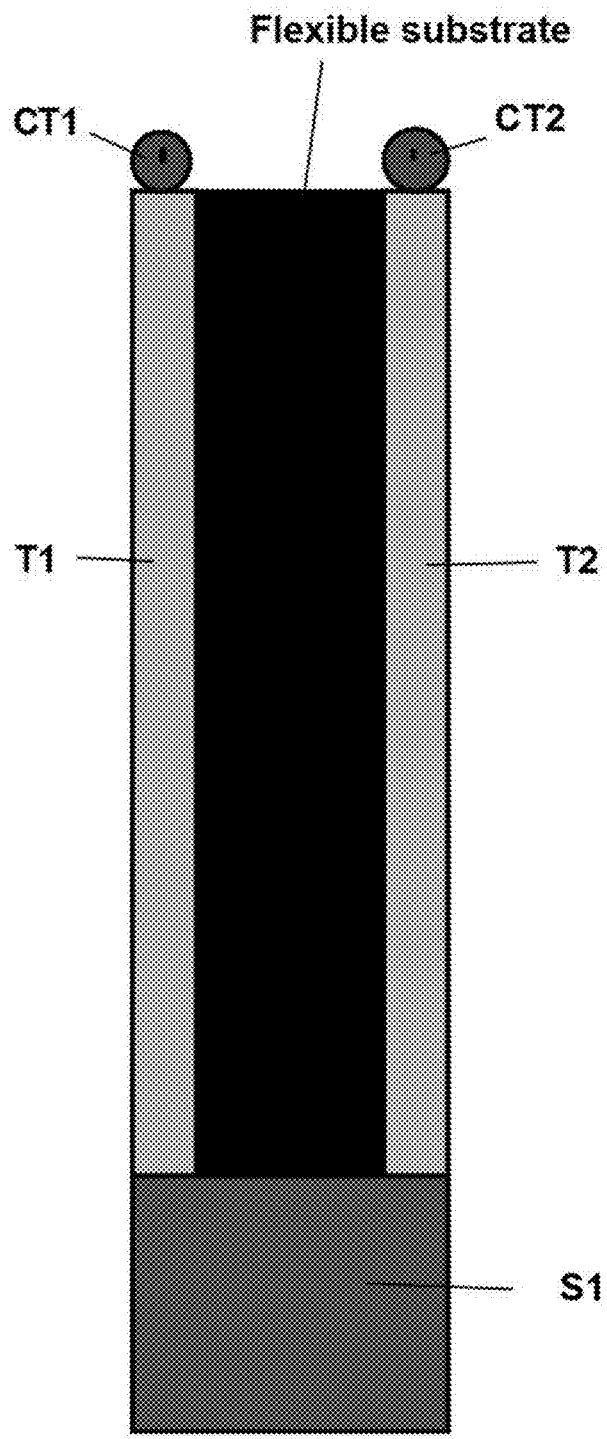
FIG. 15 shows an image illustrating an independently positionable sensor mounted to conductive leads and signal transmit terminals for placement at the discretion of a patient or care provider.

In additional applications, flexible sensors and sensor systems of the present invention may be fabricated as independently positionable sensor components and used in a variety of applications. FIG. 15 schematically illustrates an independently positionable sensor system comprising a flexible pressure sensor S1 electrically connected, via leads (not visible), to conductive traces T1 and T2, which are in turn electrically connected to conductive signal transfer terminals CT1 and CT2. The pressure sensor S1, leads, and/or conductive traces may be mounted to or associated with an underlying non-conductive flexible substrate to provide mechanical integrity to and enhance the durability of the system. It will be appreciated that this type of independent flexible sensor system may be fabricated using a wide variety of sensor sizes, and sensor functions, trace lengths, configurations, underlying substrates, and the like, and that additional and different types of sensors may be incorporated in such independent flexible sensor systems, as described above.

Figure 16A:
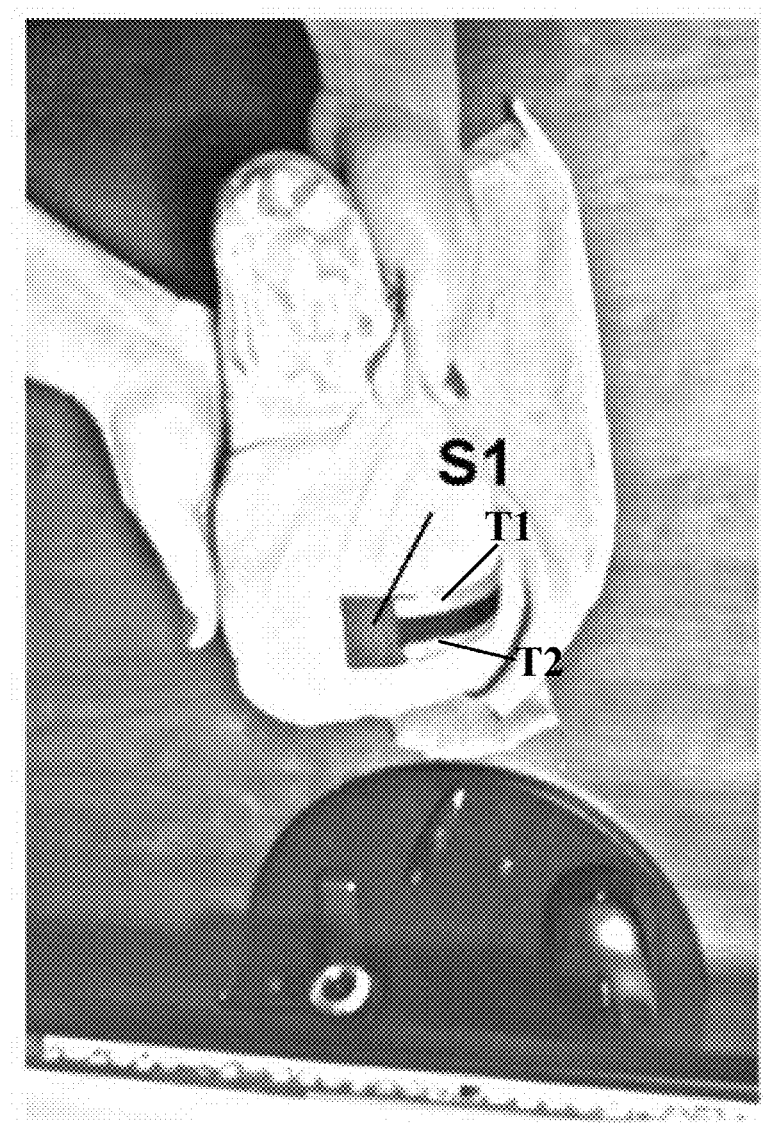
FIG. 16A illustrates the placement of an independently positionable sensor device of the type illustrated in FIG. 15 at a location (e.g., on the bottom of a patient's foot or between layers of bandages) where the patient and/or caretaker would like to monitor conditions (e.g., pressure and/or shear)
Figure 16B:
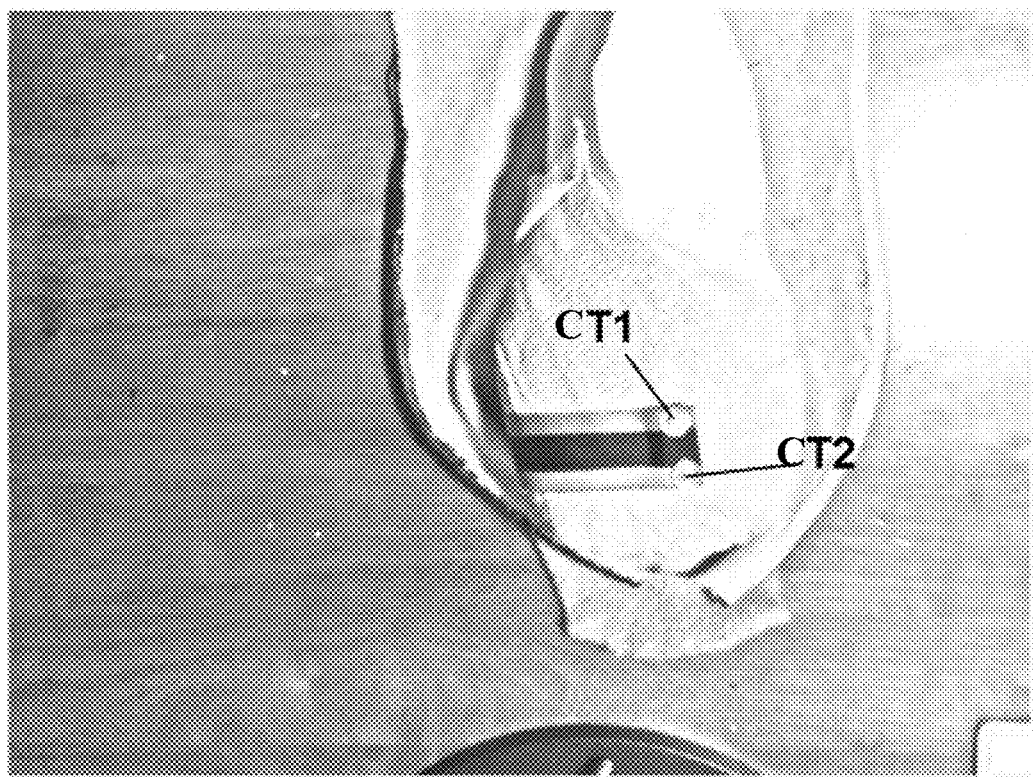
FIG. 16B illustrates signal transfer terminals connected to conductive traces connected to the sensor that are positionable, for example at the top of a patient's foot or on the exterior of a bandage, for connection to a dedicated electronic component.

One or more of these types of independently positionable flexible sensor systems may be positioned by a user, caretaker and/or clinician at a desired body site and anchored at the site using bands, wraps, or other anchoring devices. FIGS. 16A and 16B schematically illustrate the use of an independently positionable sensor system on the surface of or within a bandage wrapped around a foot. FIG. 16A shows the sensor S1 positioned as desired at a location near the bottom of the foot. The sensor S1 may be anchored to the desired sensing location, if desired, using a variety of non-conductive anchoring means such as hook and loop and other types of fasteners. Fastening means, such as hook and loop fasteners, may be mounted on or associated with a surface (or partial surface) of the sensor S1. The conductive traces T1, T2 transmit signals/data to conductive signal transfer terminals CT1, CT2 positioned or positionable at an accessible external location, such as at the top of the foot or at an ankle or lower leg position, as shown in FIG. 16B, providing access for connection of a DED and data downloading. Wraps, bands, bandages, or other anchoring systems may be wrapped around the sensor system following placement to secure the sensor system, and sensor, in place at the desired sensing location and to maintain external access to the signal transfer terminals.

Figure 17:
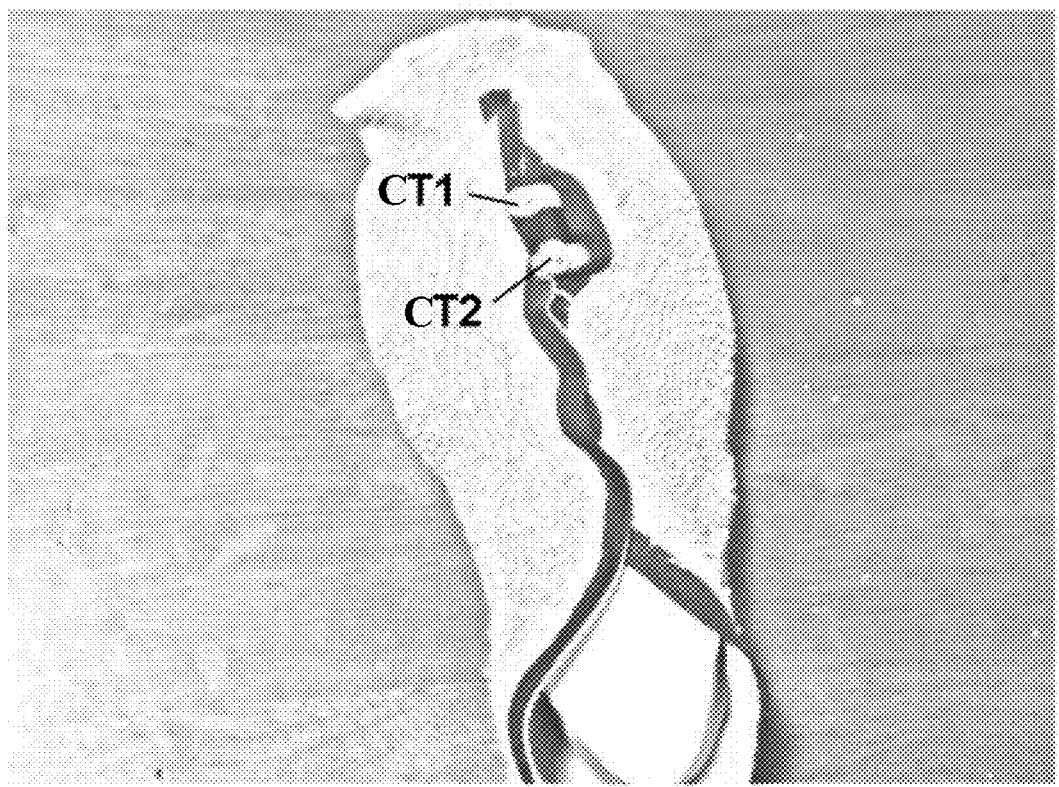
FIG. 17 shows an image illustrating one view of a sensing system using a sensor device as illustrated in FIGS. 15-16B in combination with a versatile wrap, with the conductive signal transfer terminals exposed for connection to an electronic intermediate such as a Dedicated Electronic Device (DED).

FIG. 17 illustrates a foot wrap 50 having an integrated sensor system, or employable in combination with an independently positionable sensor system such as that illustrated in FIGS. 16A and 16B positioned inside the wrap 50, between the interior surface of wrap 50 and the foot (or another body surface). The sensor is located at a desired sensing site on the foot and the conductive signal transfer terminals CT1, CT2 are positioned outside wrap 30 at a location that is accessible to a DED. It will be appreciated that while this type of wrap system is shown and described with reference to a foot wrap, it may be embodied in various types of wraps, bandages, wound and/or ulcer dressing materials and the like having a variety of sizes, configurations, and sensing capabilities. The location of the sensor(s) and conductive signal transfer terminals, and the path of the conductive traces, is highly flexible and may be adapted for sensing in many different types of applications.

Figure 18A:
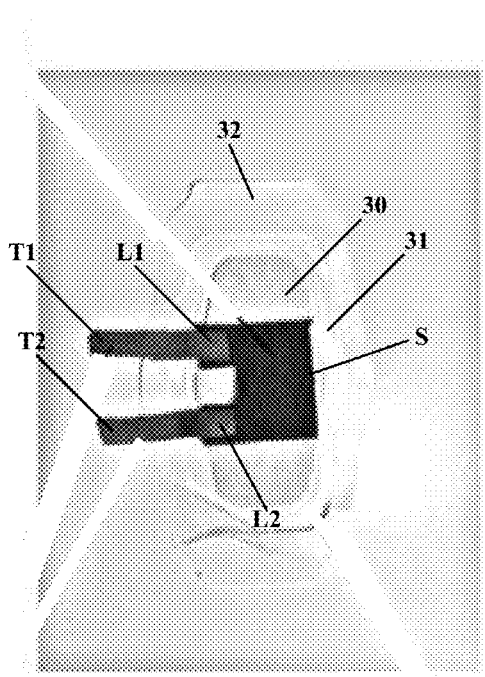
FIGS. 18A and 18B illustrate an exemplary textile sensor employing a protective, substantially liquid impermeable barrier.
Figure 18B:
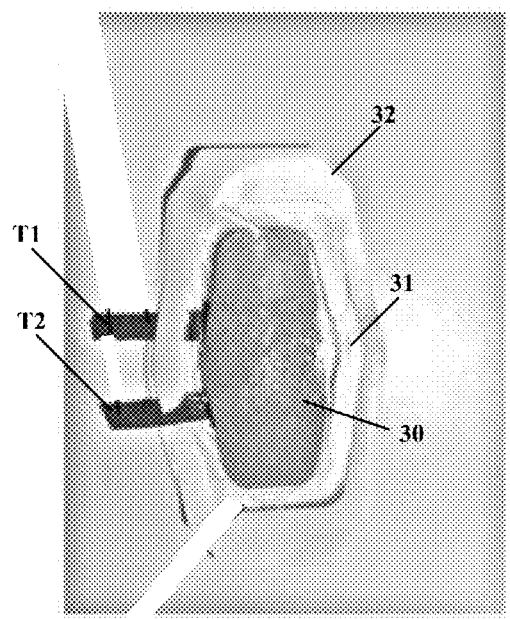

FIGS. 18A and 18B illustrate one exemplary embodiment in which one or more protective layers or materials may be provided to protect one or more sensor(s) and, optionally the associated leads, and all or portions of conductive traces, from contact with liquids, body fluids or other solutions, while preserving the core resistive features and functions of the sensor(s). A protective barrier may comprise a liquid impervious or substantially liquid impervious material, such as a generally thin plastic sheet material or a composite sheet material, that doesn't interfere with the sensing capacity of the sensor. By "substantially" liquid impervious we mean that liquid penetration of the material is insubstantial enough to affect the features and functions of the sensor(s). The protective barrier may optionally be breathable and/or gas permeable. Many such liquid impervious barrier materials are known. In some embodiments, a protective barrier may be provided on one surface of the sensor; in some embodiments, a sandwich- or envelope-type barrier that substantially seals the sensor in a substantially liquid impermeable envelope or pouch may be used.

In the embodiment shown in FIGS. 18A and 18B, barrier 30 comprises a thin, flexible sheet material and extends over and around sensor S, enclosing the sensor in a liquid impervious barrier or envelope. In the embodiment shown, surfaces or edges of barrier 30 are sealed, forming a pouch around the perimeter of sensor S at seal 31. An adhesive band 32 may be provided on one face (or both faces) of the protective barrier for mounting the sealed sensor component to an underlying surface or substrate (such as a garment, the skin of the user, or the like). Although adhesive band 32 is shown forming a peripheral band outside seal 31, it will be appreciated that adhesive components, as well as other types of mounting mechanisms, may be applied to or used in connection with protected sensor components. In the embodiments shown in FIGS. 18A and 18B, sensor S and leads L1 and L2 are encased within protective barrier 30; conductive traces T1 and T2 exit barrier 30 for attachment to conductive signal transfer terminals (not shown). Additional material layers may be provided inside and/or outside the barrier as shown in FIG. 18B to provide any desired functionality.

Figure 19:
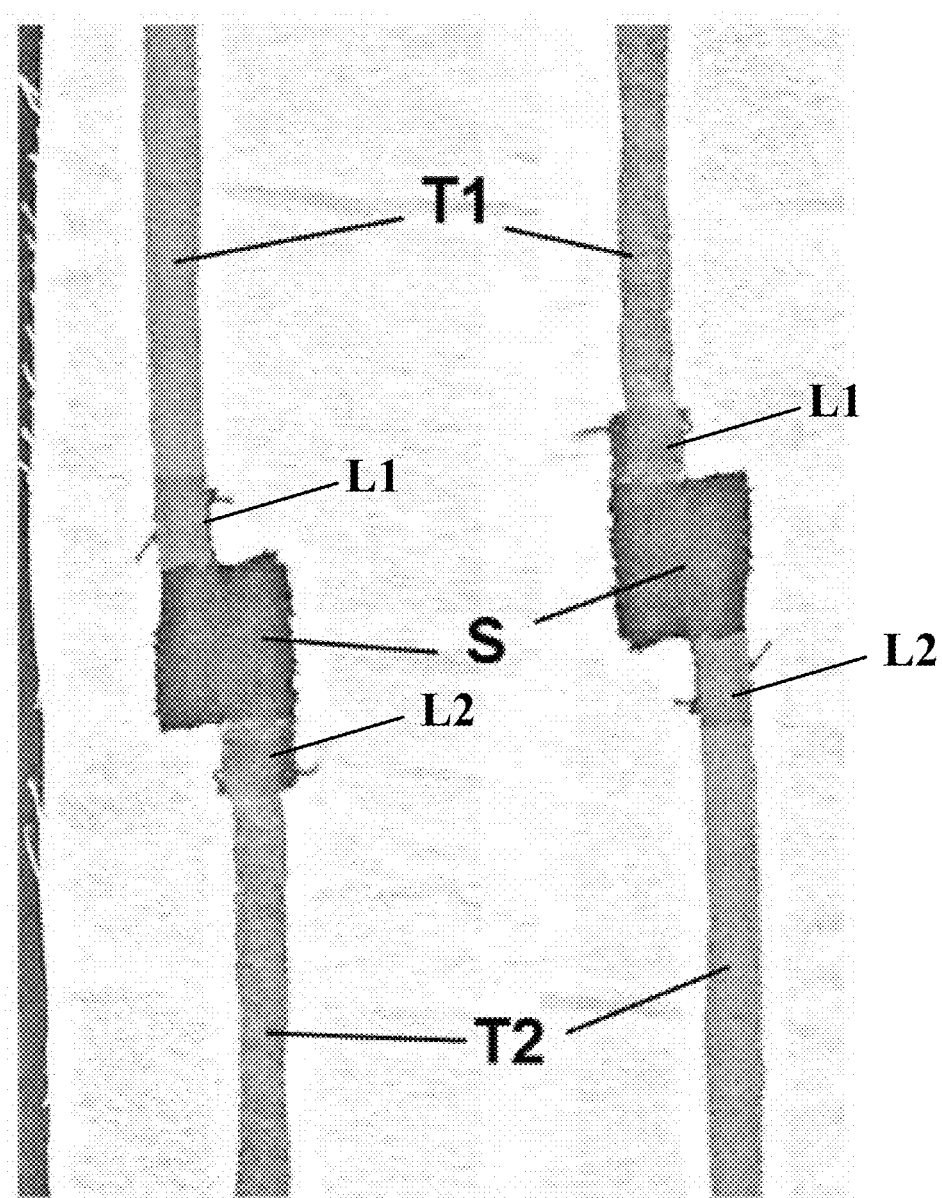
FIG. 19 schematically illustrates a sensing system having one or more sensors with leads and conductive traces terminating in terminals in a bandage or wrap form factor.

FIG. 19 schematically illustrates flexible pressure sensors S having conductive leads L1, L2 electrically connected to conductive traces T1, T2 in place on a flexible bandage 35 or on a wrap or another substrate for placement on or near wounds. The signal transfer terminals (not shown) are located on opposite sides of the bandages and may be connected to independently positionable signal receiving terminals for signal transfer. This system provides flexibility as to placement of the bandages having different sizes and configurations on different body surfaces and on body surfaces of different sizes and configurations, while permitting convenient and flexible signal transfer.

Figure 20:
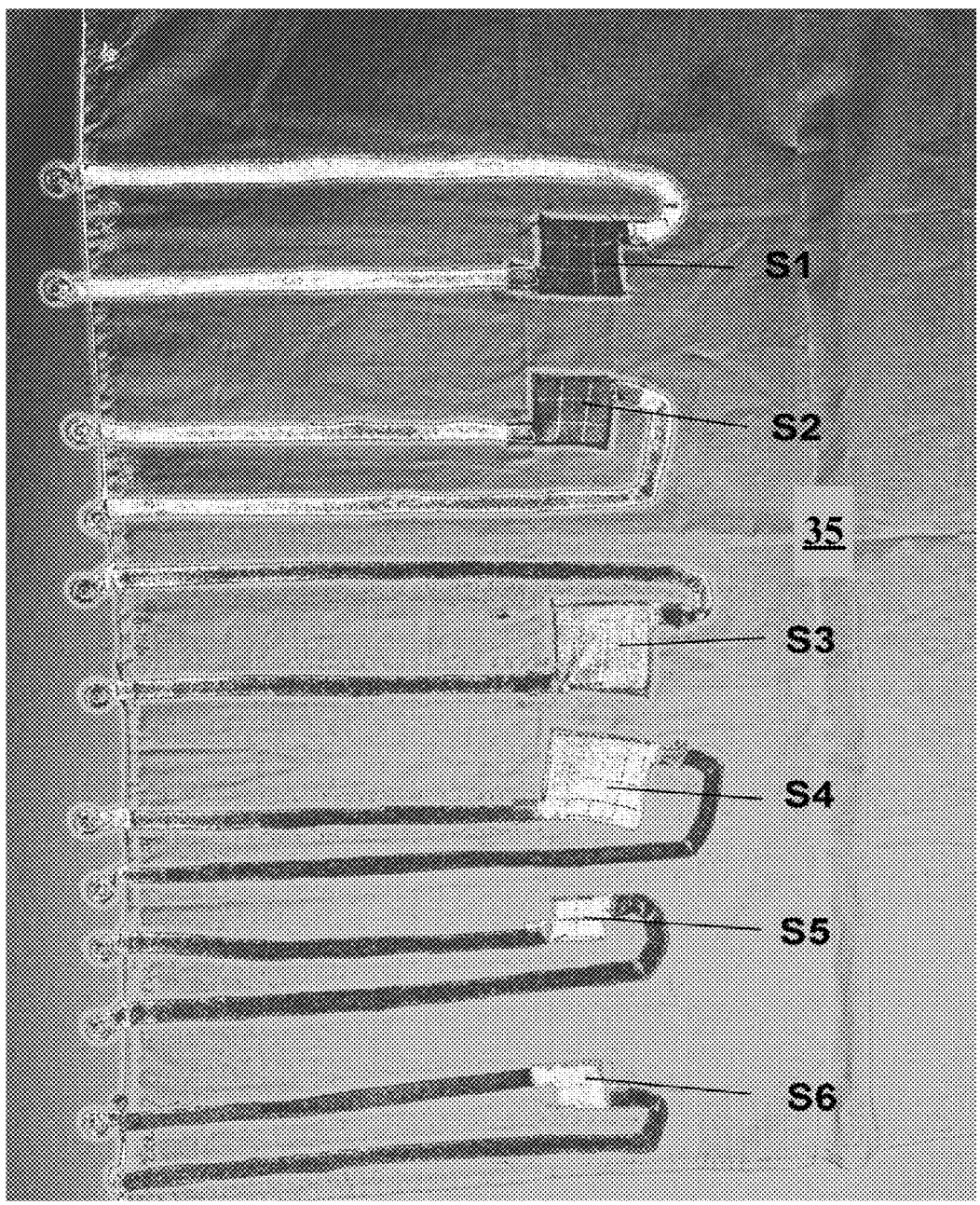
FIG. 20 schematically illustrates a fabric-based sensing system having multiple sensors with leads and conductive traces terminating in signal transmit terminals for connection to an intermediate electronic device for data collection, storage and/or processing.

FIG. 20 schematically illustrates a plurality of pressure sensors (S1-S6) mounted to/in/on, or associated with, a substrate sheet material 36 that's flexible and non-conductive. Each of the sensors S1-S6 has conductive leads electrically connected to conductive traces that terminate in signal transfer terminals located at the edge of the substrate 36. The signal transfer terminals are connectible to mating signal receiving terminals of one or more DED(s), also mountable at the edge of the substrate. In this embodiment, the DED may have a strip-like form factor for connecting to aligned signal transfer terminals. This type of sensor arrangement and system may be used, for example, in connection with various types of garments, bed sheets, chair pads, or the like, to provide data regarding pressure and/or shear at locations where a user sits, lies, or the like.

Figure 21:
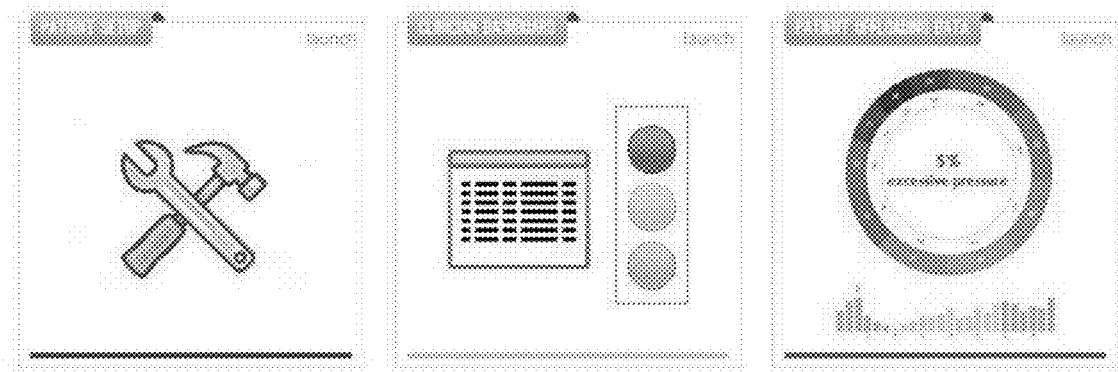
FIG. 21 schematically illustrates a patient setup protocol, clinician dashboard and patient offloading data display for monitoring wounds such as foot ulcers.

FIG. 21 schematically illustrates exemplary computer- and/or firmware- and/or software-implemented processes used by a medical monitoring system of the present invention. In some embodiments, patient setup and (optional) device authentication, program selection and the like are provided, as well as a user and/or clinician dashboard providing data output and analysis in accordance with the program selection. One specific example of output returned to the user and/or clinician is illustrated as patient offloading data, expressed as excess pressure, which provides information to the user and/or clinician as to pressure conditions (and conditions of the underlying skin and tissue) at the site of any of the pressure sensors provided in the system.

In one exemplary methodology of the present invention, a garment having one or more sensing systems as described herein is positioned on a user with sensor(s) positioned in proximity to a body area desired to be monitored, or an independently positionable sensing band, or bandage, or substrate is positioned relative to one or more body surface areas of a user desired to be monitored. A dedicated electronic device is mounted to/on or associated with exposed signal transfer terminals of the sensing system and an authentication protocol is initiated to match the garment/sensing system to the user. The authentication protocol optionally loads user data, profile information, and the like, to one or more hosted systems, such as a centralized data processing and analysis facility, a medical records facility, a caretaker system, clinician dashboard, or the like. Sensor calibration may then be conducted based on user specific information, conditions, and the like, and thresholds, limits or specific ranges, monitoring protocols, notifications, alerts, and the like may be selected by the user, a caretaker, clinician, or by the system to apply user-specific monitoring routines, parameters, and the like. Intermittent or substantially continuous user monitoring may then be initiated, with monitoring data and results provided to the user, a centralized data processing and analysis facility, a medical records facility, a caretaker system, clinician dashboard, and the like. Changes and updates to monitoring protocols may be implemented based on monitoring feedback, changes in user condition, etc.

FIGS. 22A-22L schematically illustrate exemplary device set up, calibration and monitoring criteria input, along with an exemplary clinician dashboard, a graphical representation of patient offloading data, and an exemplary sample of acquired pressure data. Processing systems and means for executing device set up and calibration, and for monitoring and reporting sensed data may reside at a computing facility that is remote from the sensing device or means and the dedicated electronic device and may comprise computer implemented systems and methods at a host computer system, a medical facility computer system, in a computing environment such as the Cloud, or the like. Reports may be displayed at the computing facility, or at any display device (e.g. a monitor, smartphone, computer, electronic healthcare system, or the like) that is capable of communicating with the computing facility.

Figure 22A:
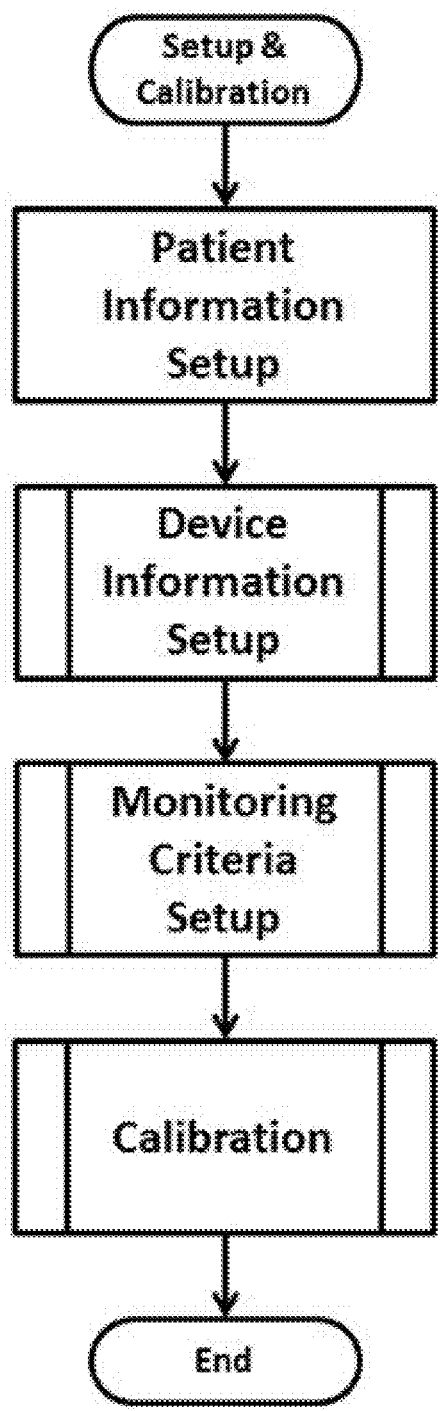

FIG. 22A schematically illustrates an exemplary setup and calibration protocol involving a patient information setup routine, a device information set up routine, a monitoring criteria set up routine and a calibration routine. A variety of different routines are available for patients having different conditions, for different device configurations, sensor types and locations, monitoring protocols, and the like. Various routines may be programmed or programmable and selectable by a user and/or by medical personnel. The routines may reside in the DED, a computing device or another bridge device, in cloud services, or the like.

Figure 22B:
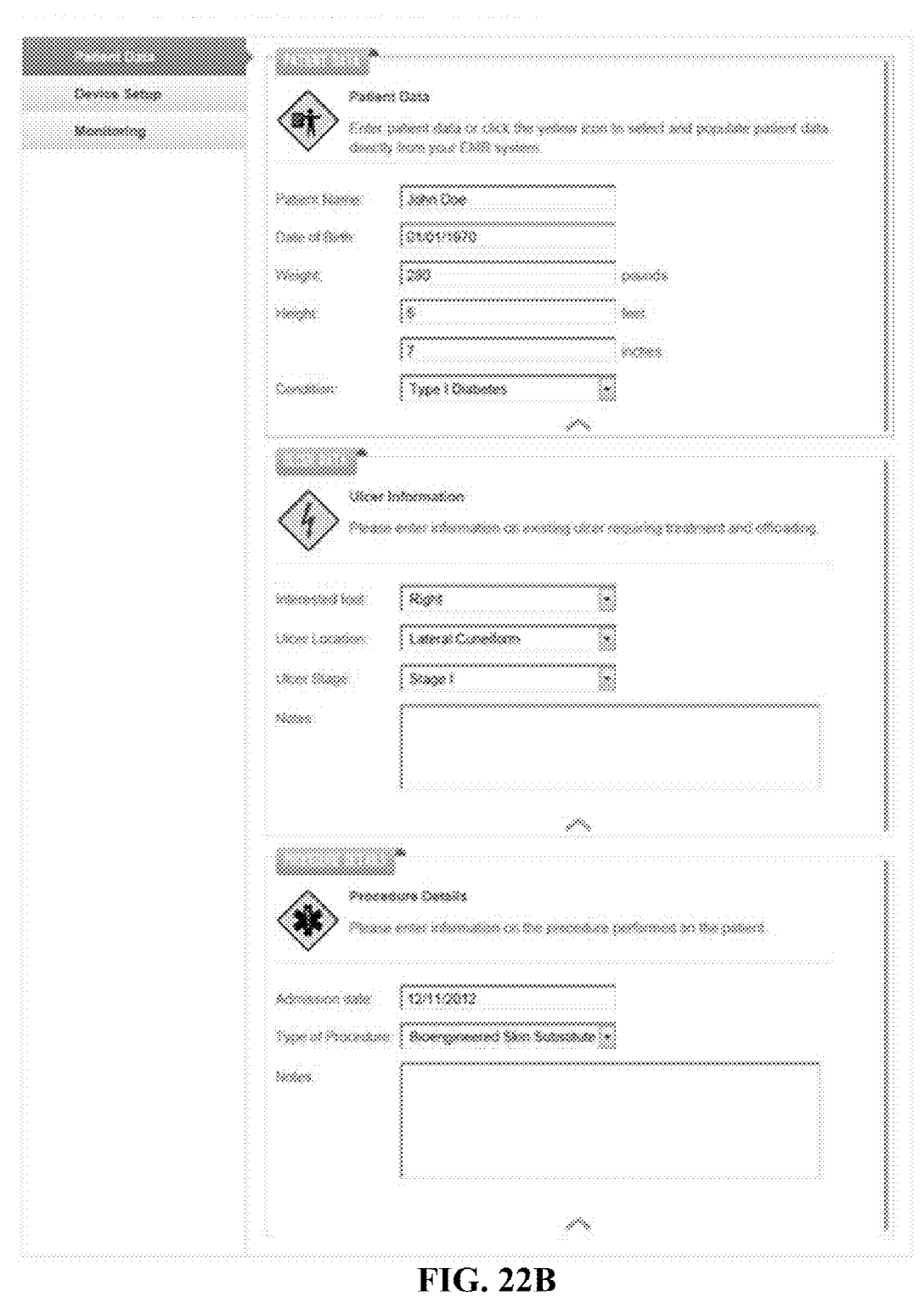

FIG. 22B schematically illustrates an exemplary patient data collection protocol forming part of the patient information setup. In this example, a doctor or another medical professional can collect and input data to associate to the specific patient/device pair. Patient identification, patient-specific information like weight, height, condition, physician, ulcer location and condition, as well as procedures undergone, hospital admissions, notes, and the like not only add information related to the specific case, but can also be used as guidance for the device calibration procedure. This information also provides meaningful data to use in aggregated views of the overall patient data.

Figure 22C:
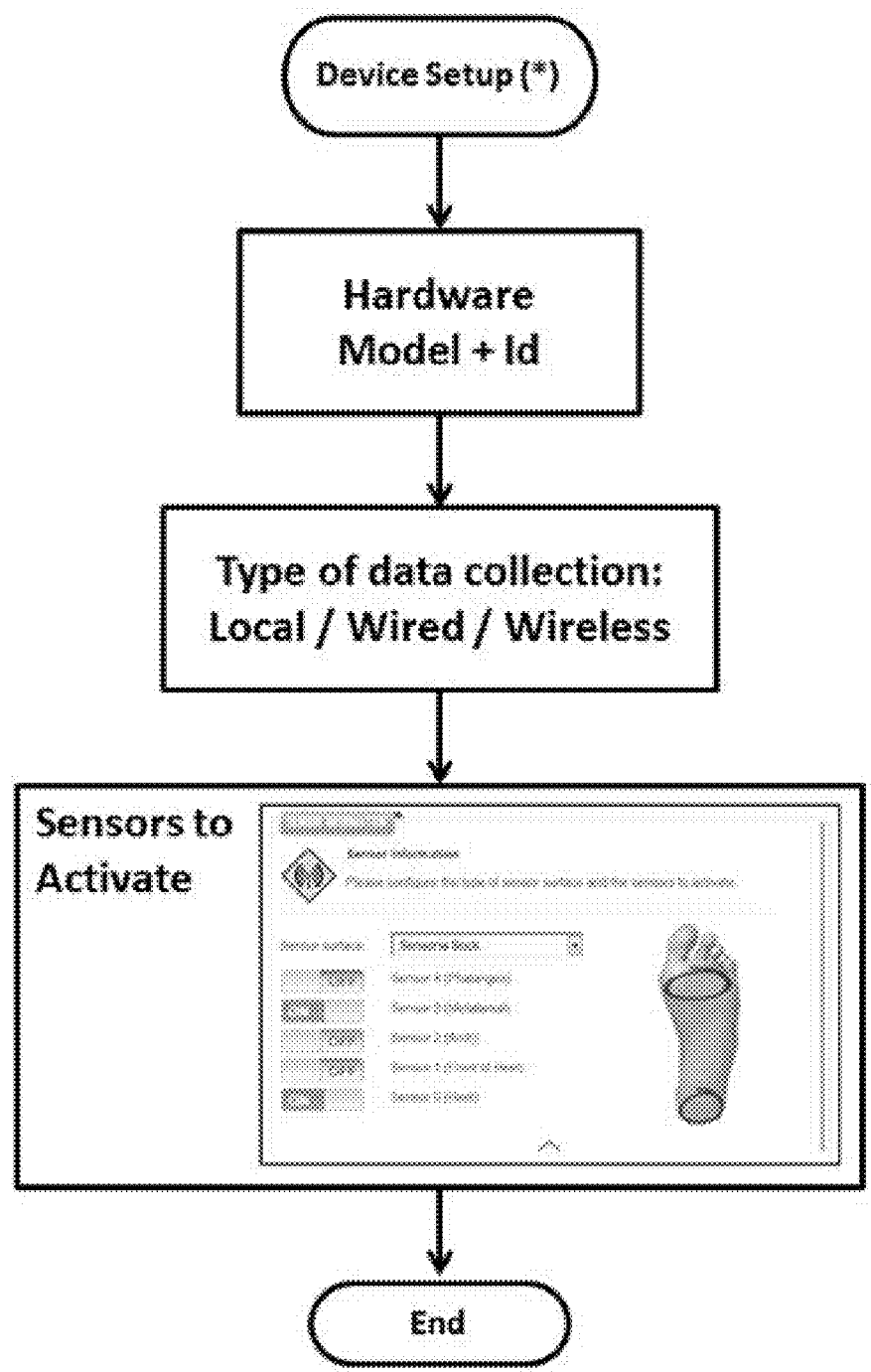
Figure 22D:
Figure 22E:
Figure 22F:
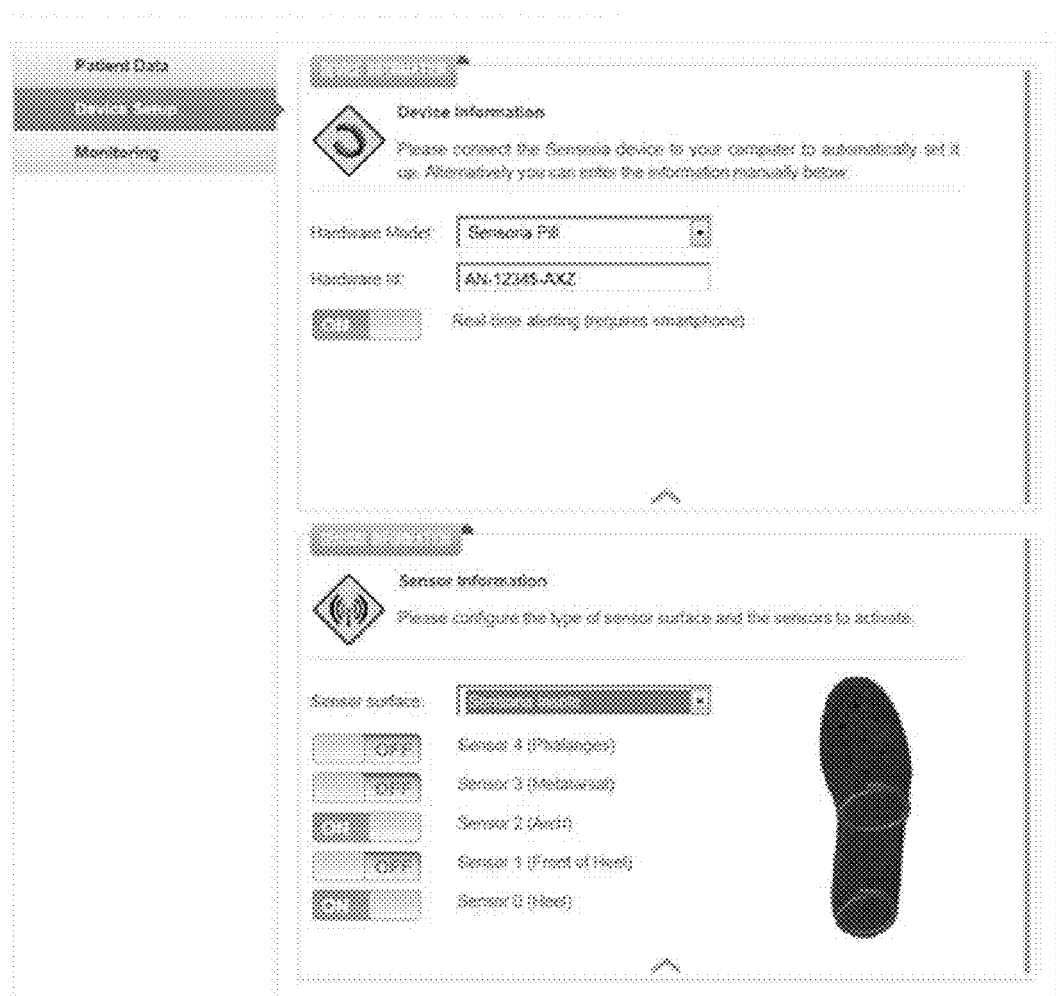

FIGS. 22C-22F schematically illustrate exemplary device setup protocols including a sensor activation selection menu. In this exemplary device setup routine, the system model number and identification is provided, along with the type of data collection. Real-time alerting and notification features may be selected. Various sensors and sensor locations may be selected and activated, while others may remain inactivated, as shown in FIGS. 22C and 22D. FIG. 22D illustrates an exemplary sensor activation menu for a sock type sensor surface, where the doctor or medical assistant can activate specific sensors in a set of 5 available for the specific example. FIG. 22E illustrates an exemplary sensor activation menu for a dressing/wrap type sensor surface, where the doctor or medical assistant can specify which type of sensor (A, B, C in the specific example) will be used for any specific patient. FIG. 22F illustrates an exemplary sensor activation menu for an insole type sensor surface, where the doctor or medical assistant can activate specific sensors in a set of 5 available for the specific example.

Figure 22G:
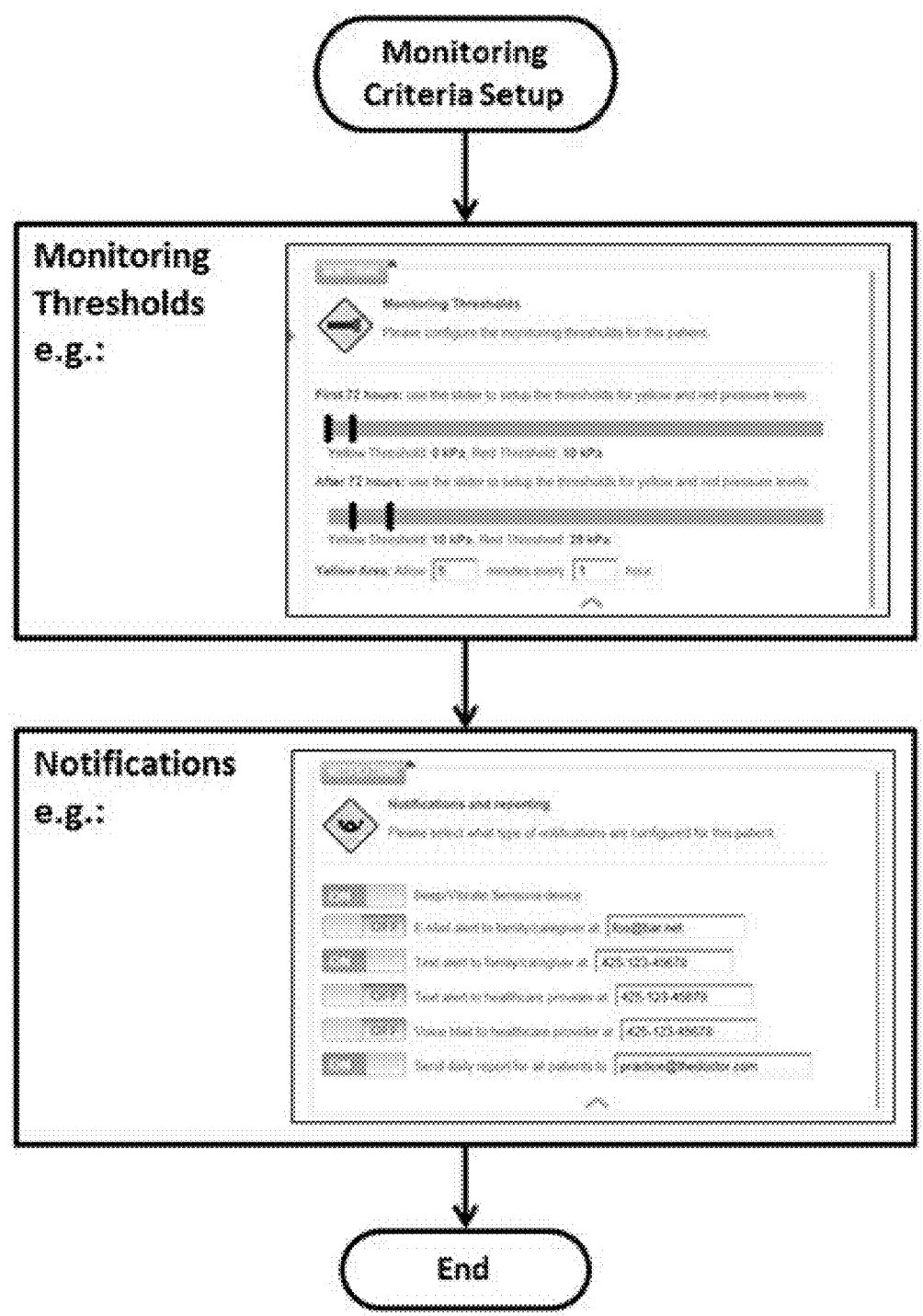
Figure 22H:
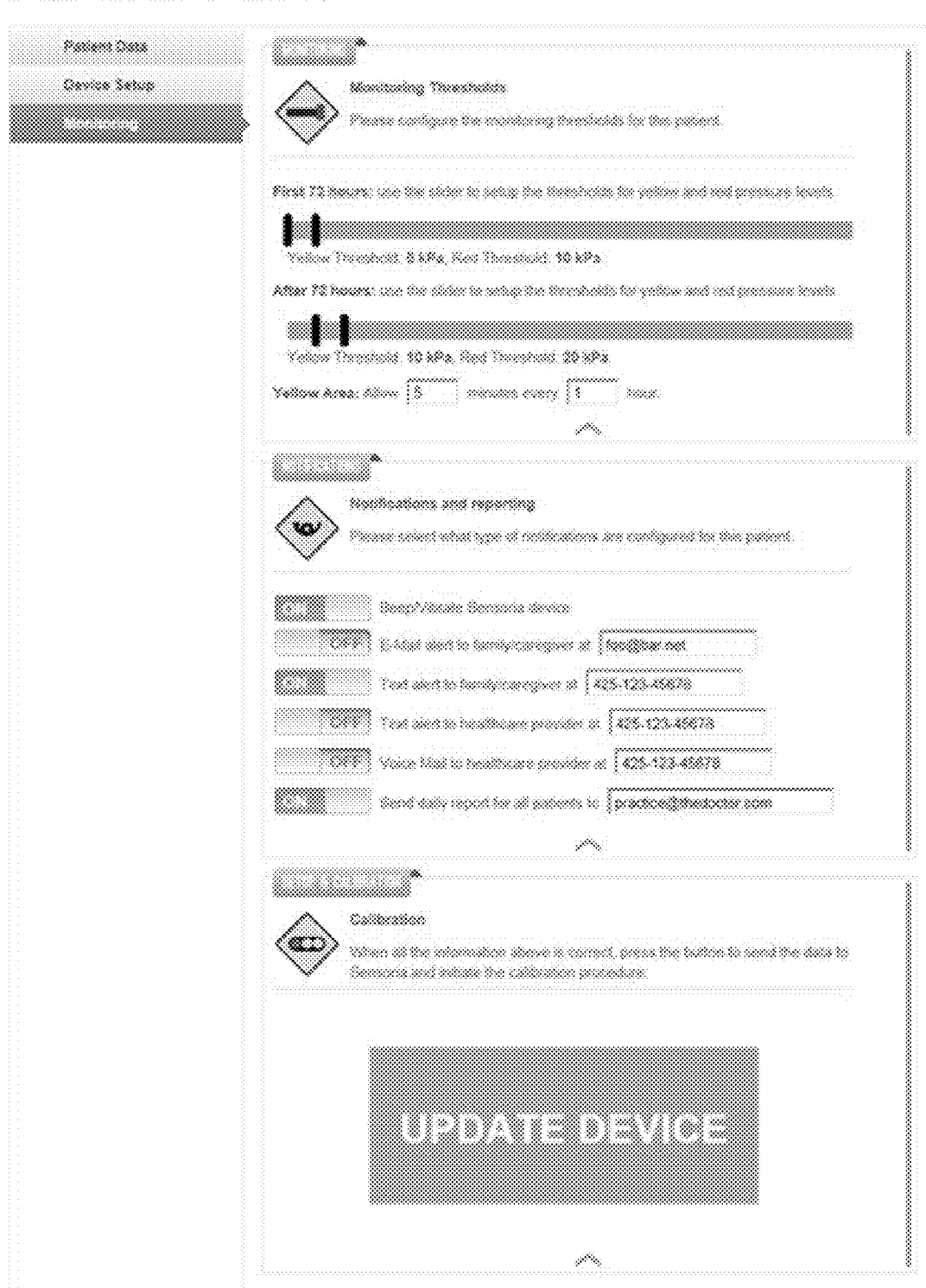

FIG. 22G schematically illustrates monitoring criteria selection menus, including a monitoring threshold selection menu and a notification selection and activation menu. FIG. 22H schematically illustrates in more detail the monitor thresholds and notification selection and activation menu. In this example, the doctor or medical assistant can define different thresholds to monitor before and after the first 72 hours post medical procedure or post sensor activation. The exemplary monitor thresholds define two levels of severity: yellow and red. In one embodiment, the yellow threshold can be surpassed for a limited period of time (for example 5 minutes every hour) without consequence: after this time-based threshold has been surpassed, the system will alert the patient or caregiver according to a notification or alert protocol. This embodiment also allows the use and selection of a red threshold that, if it is surpassed at any time, the system alerts the patient or caregiver immediately. Thresholds are managed through a hysteresis cycle, to avoid multiple alerts to be raised when the pressure level is averaging around the threshold level. The threshold levels can be preset by the parameters input for the patient and based on historical data, or defined/tuned by the doctor or medical assistant. Notifications may include vibration of the device, e-mails sent to specific addresses, text messages sent to specific phone numbers, robo-calls from an automated speech system, or the like, and the notification type, frequency, etc. may be set by the user or a medical professional as part of the monitoring routine, as shown. In some embodiments, daily reports may be sent to the doctor or caregiver for each patient using such a sensor system.

Figure 22I:
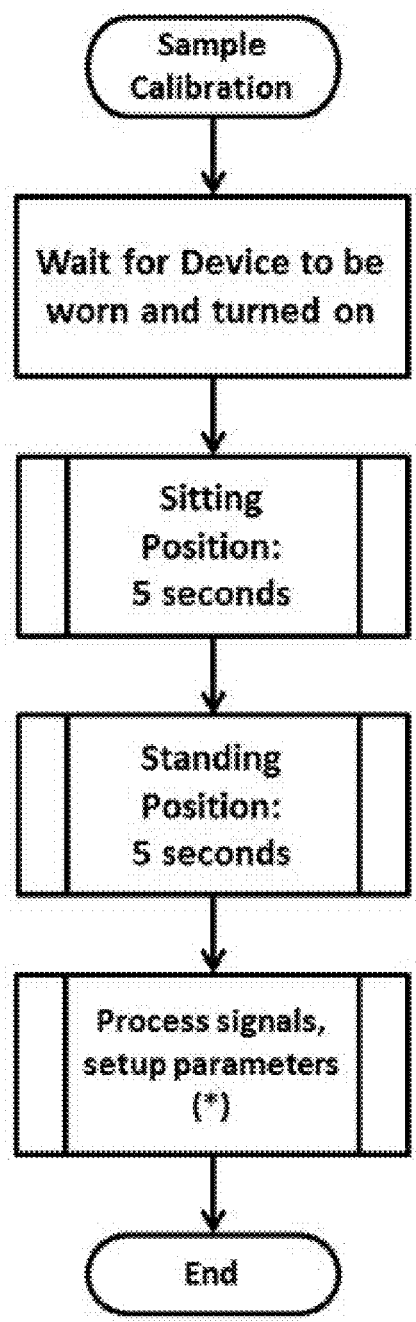

FIG. 22I schematically illustrates a sample calibration protocol for automatic set up of parameters such as filter thresholds, signal gain, voltage-to-pressure formulae, and the like, based on user-specific criteria. In this calibration, background data may be collected while the user is in various positions or doing various activities, such as sitting, standing, walking, or the like, to collect patient-specific data so that various parameters of the sensing system may be normalized to, or standardized against patient-specific "normal" parameters.

Figure 22J:
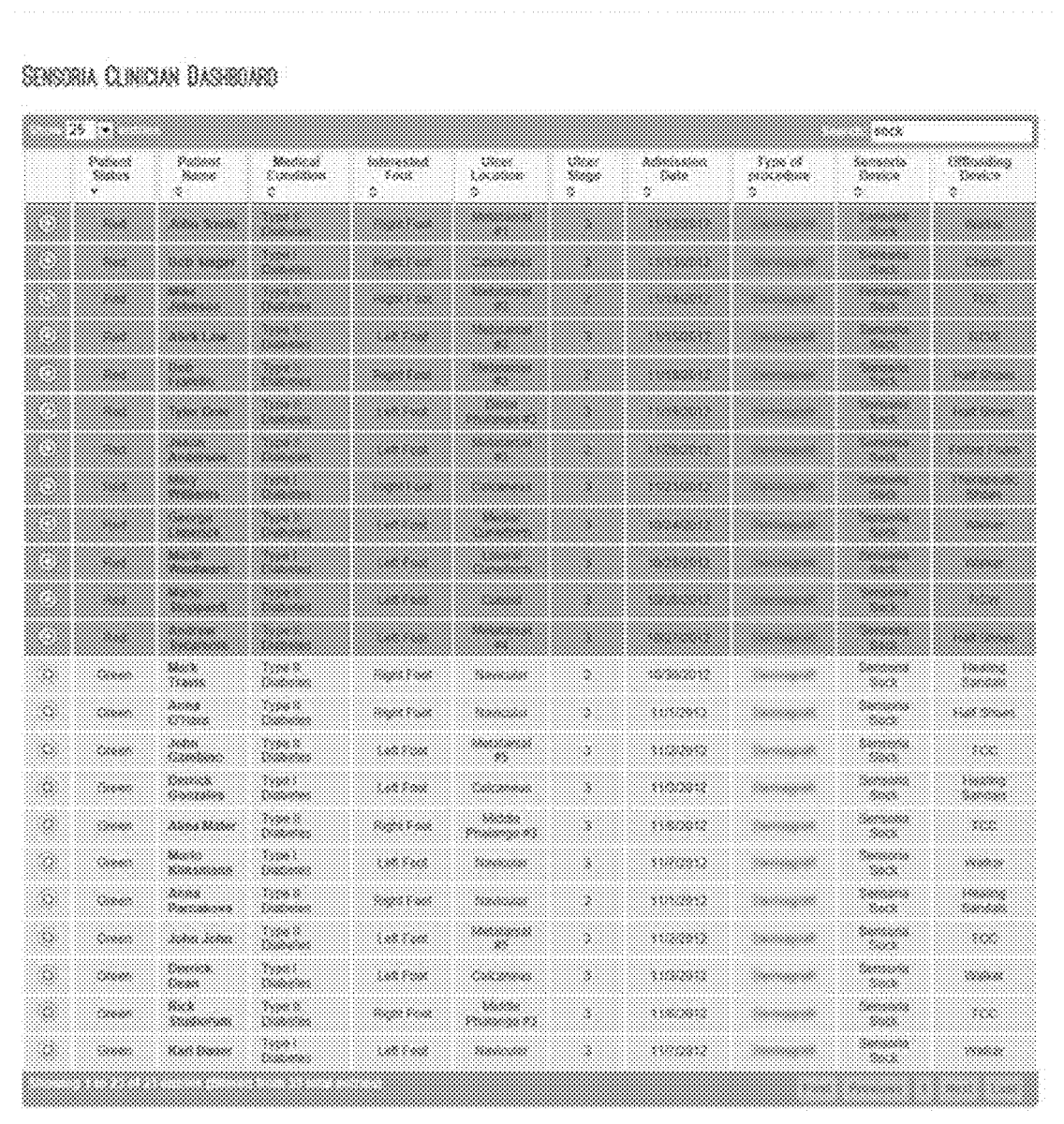

FIG. 22J illustrates an exemplary clinician dashboard displaying diabetic patient data by patient name, medical condition, foot ulcer location and condition, medical procedural history, monitoring sensor device and location, substantial real-time monitoring information, and patient status based on monitoring information. In the clinician dashboard shown, patients are categorized in red, yellow or green status based on monitoring information so that clinicians may contact and check on patients having conditions categorized in the red status and avert more serious conditions. The doctor or medical assistant can pivot the data on different "dimensions", such as type of offloading device, medical condition, ulcer location, etc. The doctor or medical assistant can also filter and sort data based on the same dimensions, to extract a view of the data aggregated for specific area of interest, both for ease of access as well as statistical purpose. For example, by analyzing this data as aggregate, specific types of offloading devices, coupled with specific types of monitoring devices used, might show a better outcome for patients with ulcers in the metatarsal area.

Figure 22K:
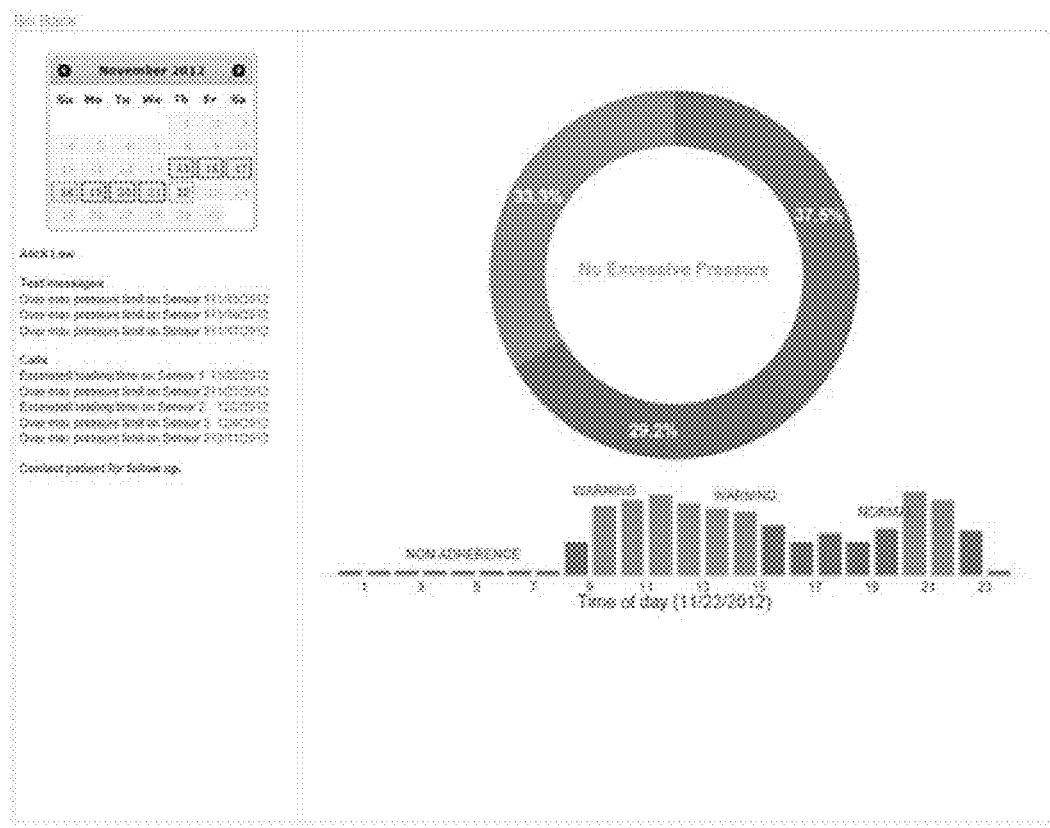

FIG. 22K schematically illustrates a patient offloading data display clearly showing excessive pressure exerted at sensing locations in real-time and historically, and providing a history of notifications and alerts provided. This data can be used by the doctor or medical assistant for the purpose of analyzing in detail the behavior of a patient, observing correlations and outcomes, as well as to provide the basis for honest conversations with patients about their behavior and how it affects the healing process. The same data can also be used to send reports to the patient, with emphasis on the good habits and positive reinforcement to improve the adherence and help the healing process.

Figure 22L:
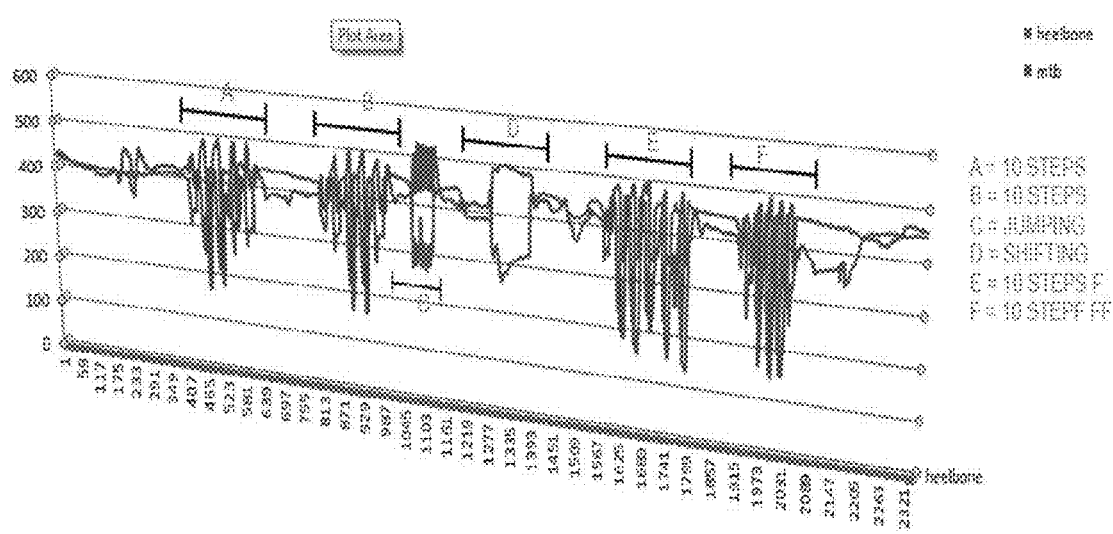

FIG. 22L schematically illustrates sensed force/pressure data collected using a sensing system as described herein with sensors located at the heelbone and at a metatarsal area, with signals in areas A and B illustrating data collected while the user walked 10 steps; signals in area C corresponding to the user jumping, signals in area D corresponding to the user shifting his weight, and signals in areas E and F illustrating data collected while the user walks additional steps following the previous activity. It will be appreciated that many other types of input and output may be provided in connection with sensor systems of the present invention, and that these diagrams are provided for purposes of illustrating specific examples of useful input and output and do not limit the invention in any way.

Medical and Athletic Monitoring

The specific examples of sensors and sensor systems described herein are applicable to patients with multiple types of foot related problems such as flat foot, injuries from accidents or military personnel injured on the battle field or patients suffering from peripheral neuropathy, and more specifically diabetic neuropathic feet wherein portions of the foot may be insensitive to pressure. The user, caretaker and/or clinician may be alerted to lack of patient adherence to off-loading guidance, areas of excess pressure and/or shear, substantially in real-time, to facilitate prevention of ulcer formation and to promote ulcer and wound healing.

In one scenario, a user/patient or an athlete wears a sock incorporating a flexible sensing system, as described. They turn on the device using a switch on the DED and put the foot in a shoe. The DED establishes a connection with one or more remote computing devices or services (e.g., via USB/Wi-Fi/Bluetooth/other medium), and pressure-related data is transferred to the remote computing device/service, where data processing and analysis takes place. Ranked recommendations related to patient adherence, performance and goal achievements, injury preventions, what/if analysis may be communicated and displayed to the patient, athlete and/or coach/caregiver in substantially real-time, allowing the patient, athlete and/or coach/caregiver to make changes to the patient's or athlete's behavior or activity in response to the sensed pressure and returned results.

Figure 23:
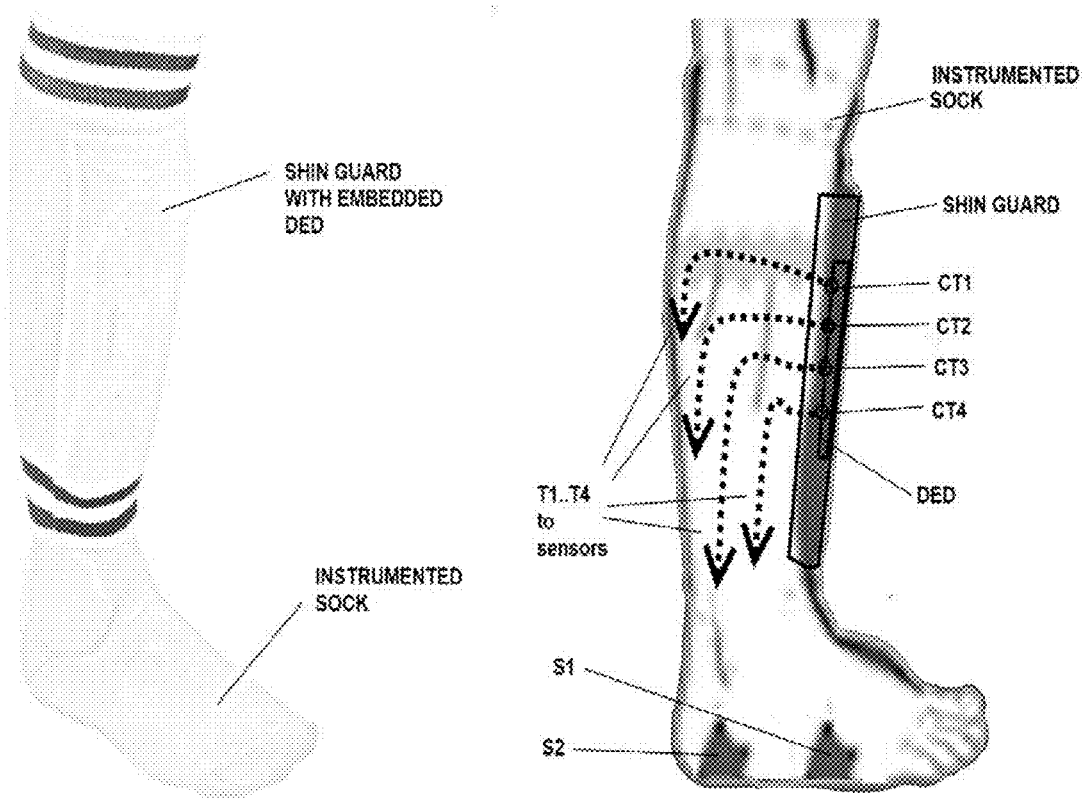
FIG. 23 shows an exemplary sensing system having sensors located in a sock, with one or more sensors electrically connected to one or more terminals, and subsequently to a dedicated electronic device located in a shin guard.

In another embodiment, systems incorporating the DED and signal receipt terminals may be mounted to and/or incorporated in or associated with other types of intermediate dedicated electronic devices, such as a protective device (e.g., a shin guard). One version of this embodiment is illustrated in FIG. 23. In this embodiment, a substrate material in the form of a sock may be equipped with one or more sensors $S1 \ldots Sn$, leads and traces $T1 \ldots Tn$ that provide signals and/or data to a set of terminals $CT1 \ldots CTn$. The terminals may comprise snaps, or connectors, mounted on the sock (male or female part) and on mating locations on a protective device, such as a shin guard device (female or male counterpart). The connectors on the sock may be located in areas where the shin guard usually overlies the sock, such that the counterpart connectors on the shin guard easily snap together and connect not only the terminals, but the sock and the shin guard. The shin guard can be manually positioned between the sock and the shin of the wearer, of be inserted in a proper fabric socket built-in the sock. In this embodiment, the shin guard is generally fabricated from a harder outer casing material and a shock absorber material on the inside. Electronic components of the dedicated electronic device (DED), as described earlier, may be provided in a core area or recess within the shin guard, well protected from excessive impact. The DED gathers data from each sensor by means of direct connections between its inputs/outputs and mating terminals $CT1 \ldots CTn$ and communicates signals and/or data to an external computing and/or bridge device, as described previously.

This type of arrangement may be used in a variety of sports that require leg and/or foot protection (e.g. soccer, hockey, football, etc.). Sensors may be placed in specific locations on a sock or another item of apparel, dependent on the type of sport and activity that is desired to be monitored. In one scenario, a soccer team may wear a sensor equipped (instrumented) sock and the shin guard with embedded DED to collect pressure data that can be processed in real-time or after the fact and extract useful statistical data for the individual and the team. For example, by placing specific sensors on the sides of the sock (foot), a software system receiving the data from the DED may be capable of determining whether the pressure signal spikes coming from the inner sensor are related to run, walk, a pass or a shot. The system may provide statistical data such as number of passes, number of shots, ball possession, etc. by means of data analysis and synthesis.

Footwear Fitting

Throughout the footwear industry, there are multiple international sizing systems and, even more importantly, a lack of standardization in shoe sizing. Sensors and sensing systems of the present invention may also be used to assist in footwear fitting. When consumers buy or order footwear in a store or online, it's difficult to assess proper fit, particularly given the large selections available and without the ability to try on footwear in their specific everyday scenario. Even when consumers shop in a store and have the ability to try footwear on, the location and the limited time and experience may not identify poorly fitting footwear. This results in lost sales opportunities and high return rates, which discourages consumers from making online purchases and significantly raises sales costs for online merchants. Being able to purchase and order footwear having confidence that it will fit well would provide substantial benefit. In 2010 three hundred and fifty million shoes were sold online, however about a third got returned. E-commerce has seen tremendous growth in recent years; however, online footwear sales make up only 12% of the total footwear market (compared to 50% for computers and 60% for books). The reason is that consumers are less comfortable buying shoes online since they cannot try on footwear before purchasing.

Pressure sensor(s) incorporated in a sock form factor, or positioned as independently positionable sensors, may be used to detect pressure on different points and areas of the foot and identify areas of discomfort. Using databases and data analysis of pressure sensors positioned on a user's foot, analytics may find and display recommended fit options for shoes, insoles and/or orthotics for specific individuals, and the individual may be alerted in real-time as to recommended fit options. The device-collected sensor data can be augmented with individualized information provided directly by the user(s), such as requested shoe type, model, or other search criteria.

In another embodiment, pressure sensors incorporated in a sock form factor, or in independently positionable sensing systems, may collect comfort and anatomic data as well as data relating to humidity, temperature, and other parameters at one or more locations on an individual's foot. The collected data may be augmented with user provided information, such as requested shoe type, model, and other search criteria, which may be processed to provide output as individual-specific recommendations and alerts.

In another embodiment, a user may take a picture of a shoe and send the image to a computing device or service (e.g. via e-mail). The footwear image may be processed and matched to footwear metadata maintained in one or more database(s) to identify potential matching footwear. A selection of related shoes, including the matching one, may be presented to the user. The selection may take in account comfort zones and foot anatomy of the current user that share common features and needs, and may rank the returned selection according to various parameters or user preferences. In one embodiment, the DED control software collects data from a sensor system to determine the anatomy of the foot. Once wearer's anatomical foot data is processed and compared to footwear data maintained in one or more databases, footwear recommendations may be displayed to the wearer, ranked according to projected fit, or other user preference(s). These systems, or similar systems, may be used to find and display ranked recommended fit options for footwear, insoles and/or orthotics.

While the present invention has been described above with reference to the accompanying drawings in which particular embodiments are shown and explained, it is to be understood that persons skilled in the art may modify the embodiments described herein without departing from the spirit and broad scope of the invention. Accordingly, the descriptions provided above are considered as being illustrative and exemplary of specific structures, aspects and features within the broad scope of the present invention and not as limiting the scope of the invention.

We claim:

1. A sensing device comprising: at least one piezoresistive fabric sensor; at least two electrically conductive fabric leads extending from each piezoresistive fabric sensor; at least one electrically conductive fabric trace connected to each conductive lead, wherein each of the electrically conductive fabric traces comprises a fabric having different properties from each of the piezoresistive fabric sensors and leads; and at least one signal transfer terminal electrically connected to each conductive fabric trace; wherein each piezoresistive fabric sensor, each conductive fabric lead, each conductive fabric trace, and each signal transfer terminal is associated with a non-electrically conductive substrate, and wherein each signal transfer terminal comprises one component of a mating magnetic fastener device.

2. The sensing device of claim 1, additionally comprising at least one additional non-fabric sensor.

3. The sensing device of claim 1, wherein the at least one piezoresistive fabric sensor is capable of sensing force exerted on the sensor.

4. The sensing device of claim 1, wherein the at least one piezoresistive fabric sensor is non-silicon-based.

5. The sensing device of claim 1, wherein the non-electrically conductive substrate is flexible and stretchable.

6. The sensing device of claim 5, wherein the non-electrically conductive substrate is in the form factor of a wearable garment.

7. The sensing device of claim 6, wherein the non-electrically conductive substrate is in the form factor of a sock.

8. The sensing device of claim 1, wherein the non-electrically conductive substrate is in the form factor of an insole.

9. The sensing device of claim 1, additionally comprising at least one sensor capable of sensing at least one of moisture and temperature.

10. The sensing device of claim 1, additionally comprising a substantially liquid impervious barrier enclosing at least the piezoresistive fabric sensor and each of the electrically conductive fabric leads.

11. A sensing device comprising a piezoresistive sensor; at least two electrically conductive leads extending from the sensor; at least one electrically conductive trace connected to each of the conductive leads; and at least one signal transfer terminal electrically connected to each of the conductive traces; wherein the sensor, the conductive leads, the conductive traces, and the signal transfer terminals are associated with a non-electrically conductive substrate, and wherein the signal transfer terminals comprise one component of a mating magnetic fastener device.

12. The sensing device of claim 11, additionally comprising a dedicated electronic device having signal receipt terminals that mate magnetically with signal transfer terminals of the sensing device and a housing component with signal processing and communications components located within the housing component.

13. The sensing device of claim 11, additionally comprising a dedicated electronic device having signal receipt terminals that mate magnetically with signal transfer terminals of the sensing device and a housing component in the form of a curved housing configured to fit partially around the lower leg or ankle of a user, with signal processing and communications components located within the housing component.

14. The sensing device of claim 11, additionally comprising a dedicated electronic device having signal receipt terminals that mate magnetically with signal transfer terminals of the sensing device and a housing component, wherein the housing component of the dedicated electronic device is configured as a shin guard, with signal processing and communications components located within the housing component.

15. The sensing device of claim 11, additionally comprising a dedicated electronic device having signal receipt terminals comprising a second component of the mating magnetic fastener device.

16. The sensing device of claim 15, wherein the dedicated electronic device additionally comprises a housing component with signal processing and communications components located within the housing component.

17. The sensing device of claim 16, wherein the housing component of the dedicated electronic device is in the form of a curved housing configured to fit partially around the lower leg or ankle of a user.

18. The sensing device of claim 15, wherein the polarity of components of the magnetic fastener device facilitate mating of the signal transfer terminals and signal receipt terminals in a predetermined orientation.

19. The sensing device of claim 15, wherein the components of the mating magnetic fastener device operate as conductive switches.

20. A system for data collection and remote monitoring of conditions at or near a body surface, comprising: at least one electrically conductive sensing device configured for positioning in direct or indirect contact with a portion of a user's body surface and having signal transfer terminals associated with a flexible, non-conductive substrate; a dedicated electronic device having signal processing and communications components and signal receipt terminals that receive signals from the signal transfer terminals of the sensing device; and a remote computing facility configured to receive data from the dedicated electronic device and execute data analysis in accordance with at least one of programmed and programmable instructions and routines, wherein the signal transfer terminals and the signal receipt terminals are detachably and magnetically matable.

21. The system of claim 20, wherein the polarity of magnetic components of the signal transfer terminals and the signal receipt terminals is configured to facilitate mating of the signal transfer terminals and signal receipt terminals in a predetermined orientation.

22. The system of claim 20, wherein components of the signal transfer terminals and the signal receipt terminals operate as conductive magnetic snap switches.

* * * * *